US012458348B2

(12) United States Patent
Shelton, IV et al.

(10) Patent No.: US 12,458,348 B2
(45) Date of Patent: Nov. 4, 2025

(54) DEFLECTABLE FIRING MEMBER FOR SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US); Gregory J. Bakos, Mason, OH (US); Michael J. Vendely, Lebanon, OH (US); Adam D. Hensel, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 109 days.

(21) Appl. No.: 17/402,759

(22) Filed: Aug. 16, 2021

(65) Prior Publication Data

US 2023/0052307 A1 Feb. 16, 2023

(51) Int. Cl.
*A61B 17/072* (2006.01)
*A61B 17/00* (2006.01)

(52) U.S. Cl.
CPC .. *A61B 17/072* (2013.01); *A61B 2017/00367* (2013.01)

(58) Field of Classification Search
CPC ........ A61B 17/072; A61B 2017/00367; A61B 2017/00323; A61B 2017/00309; A61B 2017/00314; A61B 2017/2927; A61B 34/30; A61B 17/07207; A61B 2034/306
USPC ...................................................... 227/175.1
See application file for complete search history.

(56) References Cited

U.S. PATENT DOCUMENTS

| | | | |
|---|---|---|---|
| 5,129,570 | A | 7/1992 | Schulze et al. |
| 7,404,508 | B2 | 7/2008 | Smith et al. |
| 7,434,715 | B2 | 10/2008 | Shelton, IV et al. |
| 7,721,930 | B2 | 5/2010 | McKenna et al. |
| 7,810,692 | B2 | 10/2010 | Hall et al. |
| 7,832,408 | B2 | 11/2010 | Shelton, IV et al. |

(Continued)

FOREIGN PATENT DOCUMENTS

| | | | |
|---|---|---|---|
| EP | 3509505 | A1 | 7/2019 |
| WO | WO 2015/153642 | A1 | 10/2015 |

(Continued)

OTHER PUBLICATIONS

U.S. Appl. No. 17/088,941, entitled "Surgical Stapler End Effector Sled Having Cartridge Wall Support Feature," filed Nov. 4, 2020.

(Continued)

*Primary Examiner* — Veronica Martin
(74) *Attorney, Agent, or Firm* — FROST BROWN TODD LLP

(57) ABSTRACT

A surgical stapling instrument includes a shaft assembly, an end effector, and a flexible firing member. The end effector includes a driving assembly translatable distally relative to a first jaw and a second jaw to thereby transition the first and second jaws from an open state to a closed state. The flexible firing member is configured to selectively advance the driving assembly distally and retract the driving assembly proximally. The flexible firing member includes a plurality of segments, at least one axial force transmission feature configured to transmit axial forces between the segments, and at least one lateral alignment feature configured to resist lateral misalignment of the segments.

20 Claims, 18 Drawing Sheets

(56) References Cited

U.S. PATENT DOCUMENTS

| | | | |
|---|---|---|---|
| 7,845,537 B2 | 12/2010 | Shelton, IV et al. | |
| 8,083,120 B2 | 12/2011 | Shelton, IV et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,708,213 B2 | 4/2014 | Shelton, IV et al. | |
| 9,060,770 B2 | 6/2015 | Shelton, IV et al. | |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,487 B2 | 12/2017 | Dachs, II | |
| 10,011,018 B2 | 7/2018 | McGrogan et al. | |
| 10,092,292 B2 | 10/2018 | Boudreaux et al. | |
| 10,307,170 B2 | 6/2019 | Parfett et al. | |
| 10,485,621 B2 | 11/2019 | Morrissette et al. | |
| 10,537,400 B2 | 1/2020 | Dachs, II et al. | |
| 10,610,313 B2 | 4/2020 | Bailey et al. | |
| 10,667,809 B2 | 6/2020 | Bakos et al. | |
| 10,806,530 B2 | 10/2020 | Liao et al. | |
| 10,863,988 B2 | 12/2020 | Patel et al. | |
| 11,020,138 B2 | 6/2021 | Ragosta | |
| 11,026,755 B2 | 6/2021 | Weir et al. | |
| 11,076,926 B2 | 8/2021 | Ragosta et al. | |
| 11,147,552 B2 | 10/2021 | Burbank et al. | |
| 11,166,773 B2 | 11/2021 | Ragosta et al. | |
| 11,234,700 B2 | 2/2022 | Ragosta et al. | |
| 11,259,884 B2 | 3/2022 | Burbank | |
| 2006/0185682 A1 | 8/2006 | Marczyk | |
| 2011/0028991 A1* | 2/2011 | Ikeda | A61B 34/71 606/130 |
| 2012/0209314 A1 | 8/2012 | Weir et al. | |
| 2015/0297228 A1 | 10/2015 | Huitema et al. | |
| 2016/0361126 A1 | 12/2016 | Schena et al. | |
| 2017/0020617 A1 | 1/2017 | Weir et al. | |
| 2017/0265865 A1 | 9/2017 | Burbank | |
| 2017/0265954 A1 | 9/2017 | Burbank et al. | |
| 2017/0333037 A1 | 11/2017 | Wellman et al. | |
| 2018/0008265 A1 | 1/2018 | Hatanaka et al. | |
| 2018/0168756 A1 | 6/2018 | Liao et al. | |
| 2018/0271608 A1 | 9/2018 | Ragosta et al. | |
| 2018/0310935 A1 | 11/2018 | Wixey | |
| 2018/0325606 A1 | 11/2018 | Weir et al. | |
| 2018/0344419 A1 | 12/2018 | Dachs, II et al. | |
| 2019/0038371 A1 | 2/2019 | Wixey et al. | |
| 2019/0076142 A1 | 3/2019 | Wixey | |
| 2019/0076143 A1 | 3/2019 | Smith | |
| 2019/0117247 A1* | 4/2019 | Kim | A61B 34/74 |
| 2019/0167266 A1 | 6/2019 | Patel et al. | |
| 2019/0192158 A1* | 6/2019 | Scott | A61B 17/2833 |
| 2019/0200989 A1 | 7/2019 | Burbank et al. | |
| 2019/0239967 A1* | 8/2019 | Ragosta | A61B 17/07207 |
| 2019/0262088 A1 | 8/2019 | Burbank | |
| 2020/0138529 A1 | 5/2020 | Ragosta et al. | |
| 2020/0222044 A1* | 7/2020 | Baxter, III | A61B 17/0644 |
| 2020/0397430 A1 | 12/2020 | Patel et al. | |
| 2020/0405301 A1 | 12/2020 | Shelton, IV et al. | |
| 2021/0393340 A1 | 12/2021 | Beckman et al. | |
| 2021/0401433 A1 | 12/2021 | Freidel et al. | |

FOREIGN PATENT DOCUMENTS

| | | |
|---|---|---|
| WO | WO 2017/083125 A1 | 5/2017 |
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/085529 A2 | 5/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

U.S. Appl. No. 17/402,674, entitled "Methods of Operating a Robotic Surgical Stapler," filed Aug. 16, 2021.

U.S. Appl. No. 17/402,675, entitled "Multi-Threshold Motor Control Algorithm for Powered Surgical Stapler," filed Aug. 16, 2021.

U.S. Appl. No. 17/402,677, entitled "Variable Response Motor Control Algorithm for Powered Surgical Stapler," filed Aug. 16, 2021.

U.S. Appl. No. 17/402,679, entitled "Powered Surgical Stapler Having Independently Operable Closure and Firing Systems," filed Aug. 16, 2021.

U.S. Appl. No. 17/402,695, entitled "Firing System Features for Surgical Stapler," filed Aug. 16, 2021.

U.S. Appl. No. 17/402,701, entitled "Multiple-Sensor Firing Lockout Mechanism for Powered Surgical Stapler," filed Aug. 16, 2021.

U.S. Appl. No. 17/402,703, entitled "Proximally Located Firing Lockout Mechanism for Surgical Stapler," filed Aug. 16, 2021.

U.S. Appl. No. 17/402,720, entitled "Cartridge-Based Firing Lockout Mechanism for Surgical Stapler," filed Aug. 16, 2021.

U.S. Appl. No. 17/402,732, entitled "Multi-Position Restraining Member for Sled Movement," filed Aug. 16, 2021.

U.S. Appl. No. 17/402,738, entitled "Firing Member Tracking Feature for Surgical Stapler," filed Aug. 16, 2021.

U.S. Appl. No. 17/402,744, entitled "Adjustable Power Transmission Mechanism for Powered Surgical Stapler," filed Aug. 16, 2021.

U.S. Appl. No. 17/402,749, entitled "Firing Bailout System for Powered Surgical Stapler," filed Aug. 16, 2021.

International Search Report and Written Opinion dated Nov. 22, 2022 for Application No. PCT/IB2022/057616, 12 pgs.

* cited by examiner

DEFLECTABLE FIRING MEMBER FOR SURGICAL STAPLER

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
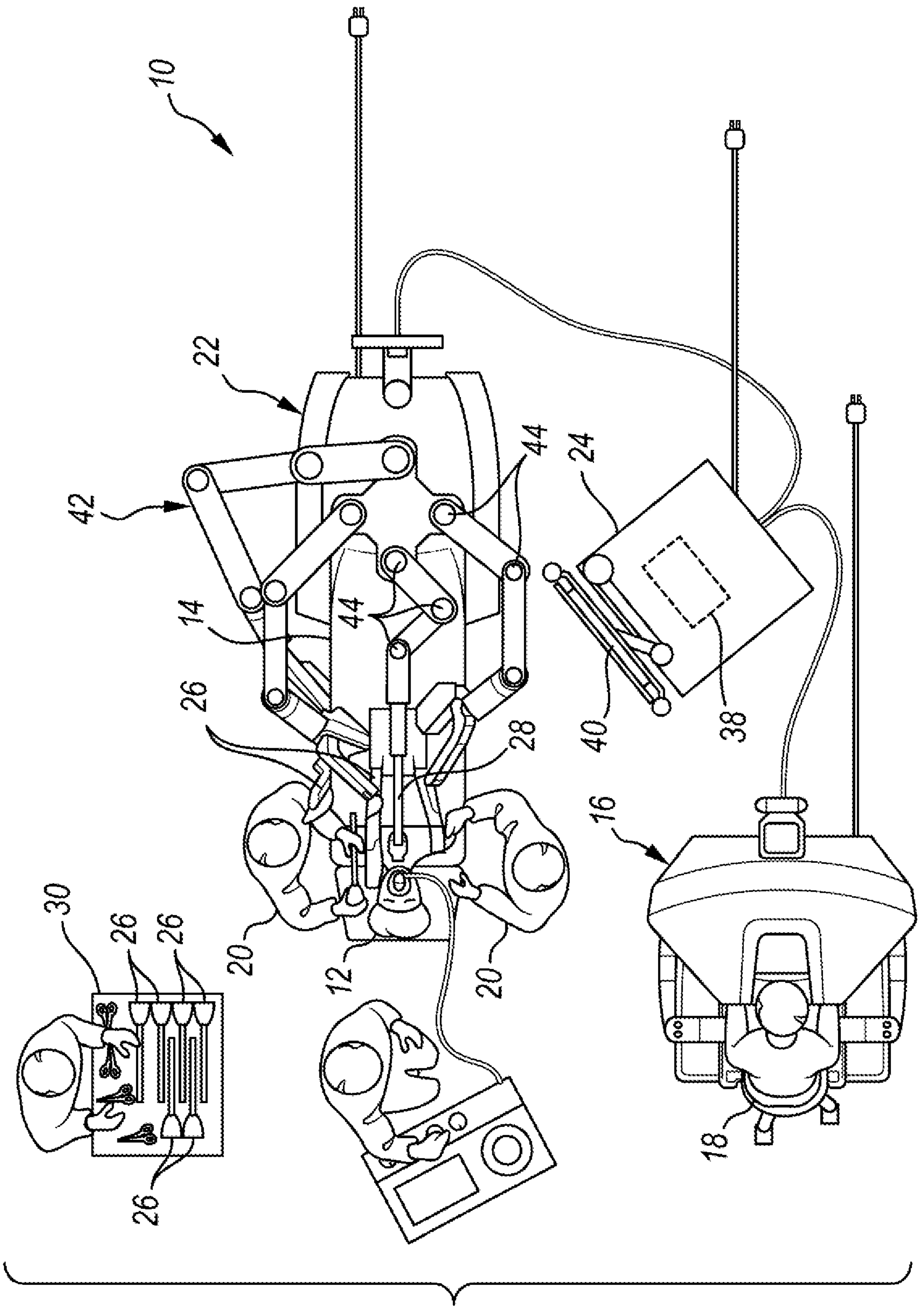
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018, issued as U.S. Pat. No. 11,076,929 on Aug. 3, 2021; U.S. Pub. No. 2018/0325606, entitled "Systems and Methods for Operating an End Effector," published Nov. 15, 2018, issued as U.S. Pat. No. 11,026,755 on Jun. 8, 2021; U.S. Pub. No. 2019/0200989, entitled "Stapler Reload Detection and Identification," published Jul. 4, 2019, issued as U.S. Pat. No. 11,364,029 on Jun. 21, 2022; U.S. Pub. No. 2019/0239967, entitled "Stapler Beam Architecture," published Aug. 8, 2019, issued as U.S. Pat. No. 11,166,773 on Nov. 9, 2021; U.S. Pub. No. 2019/0262088, entitled "Robotic Surgical Stapler Assembly Configured to Use Stapler Reload," published Aug. 29, 2019, issued as U.S. Pat. No. 11,259,884 on Mar. 1, 2022; U.S. Pub. No. 2019/0239877, entitled "Wrist Architecture," published Aug. 8, 2019, issued as U.S. Pat. No. 11,234,700 on Feb. 1, 2022; U.S. Pub. No. 2019/0201150, entitled "Push-Pull Surgical Instrument End Effector Actuation Using Flexible Tension Member," published Jul. 4, 2019, issued as U.S. Pat. No. 11,020,138 on Jun. 1, 2021; U.S. Pub. No. 2019/0282233, entitled "Stapler Cartridge With an Integral Knife," published Sep. 19, 2019, issued as U.S. Pat. No. 11,147,552 on Oct. 19, 2021; U.S. Pub. No. 2019/0262088, entitled "Robotic Surgical Stapler Assembly Configured to Use Stapler Reload," published Aug. 29, 2019, issued as U.S. Pat. No. 11,259,884 on Mar. 1, 2022; U.S. Pub. No. 2020/0138529, entitled "Locking System for Medical Device Drive System," published May 7, 2020, issued as U.S. Pat. No. 11,633,239 on Apr. 25, 2023; and/or U.S. Pub. No. 2020/0397430, entitled "Surgical Instrument With Lockout Mechanism," published Dec. 24, 2020, issued as U.S. Pat. No. 11,439,390 on Sep. 13, 2022. The disclosure of each of the above-cited U.S. patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
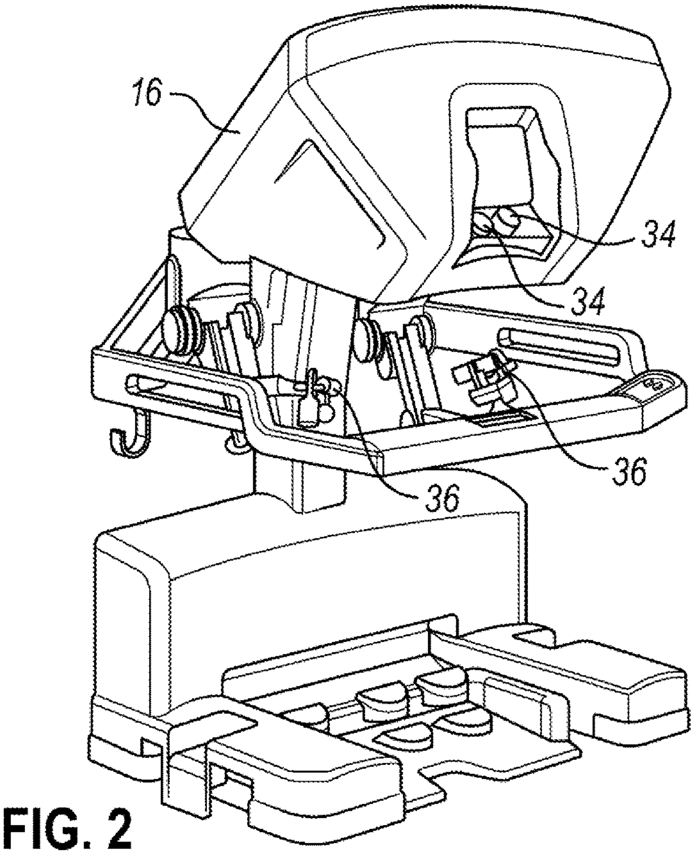
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
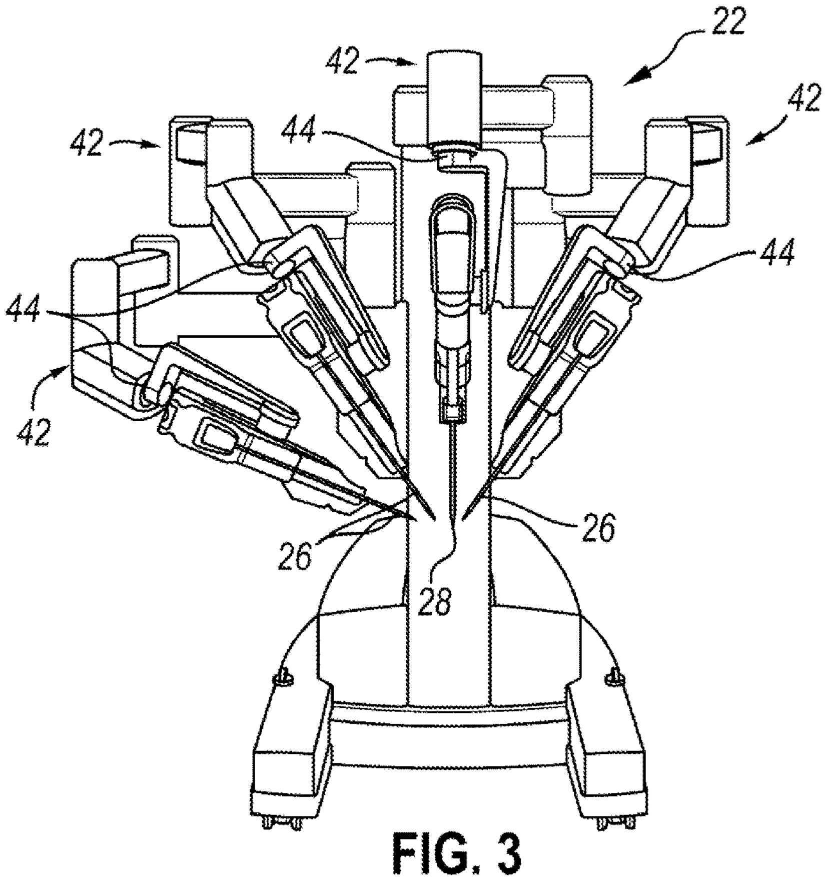
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
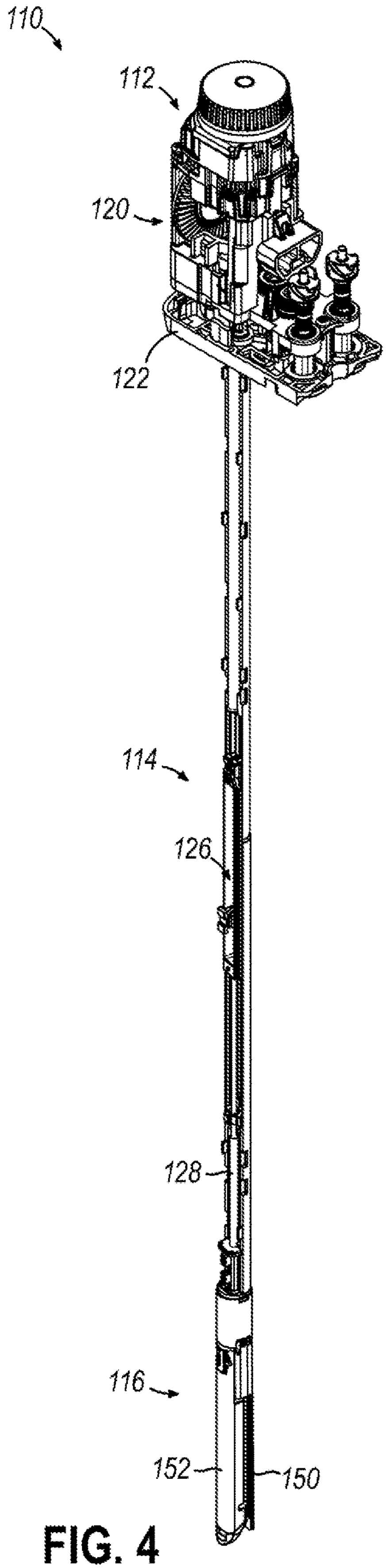
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
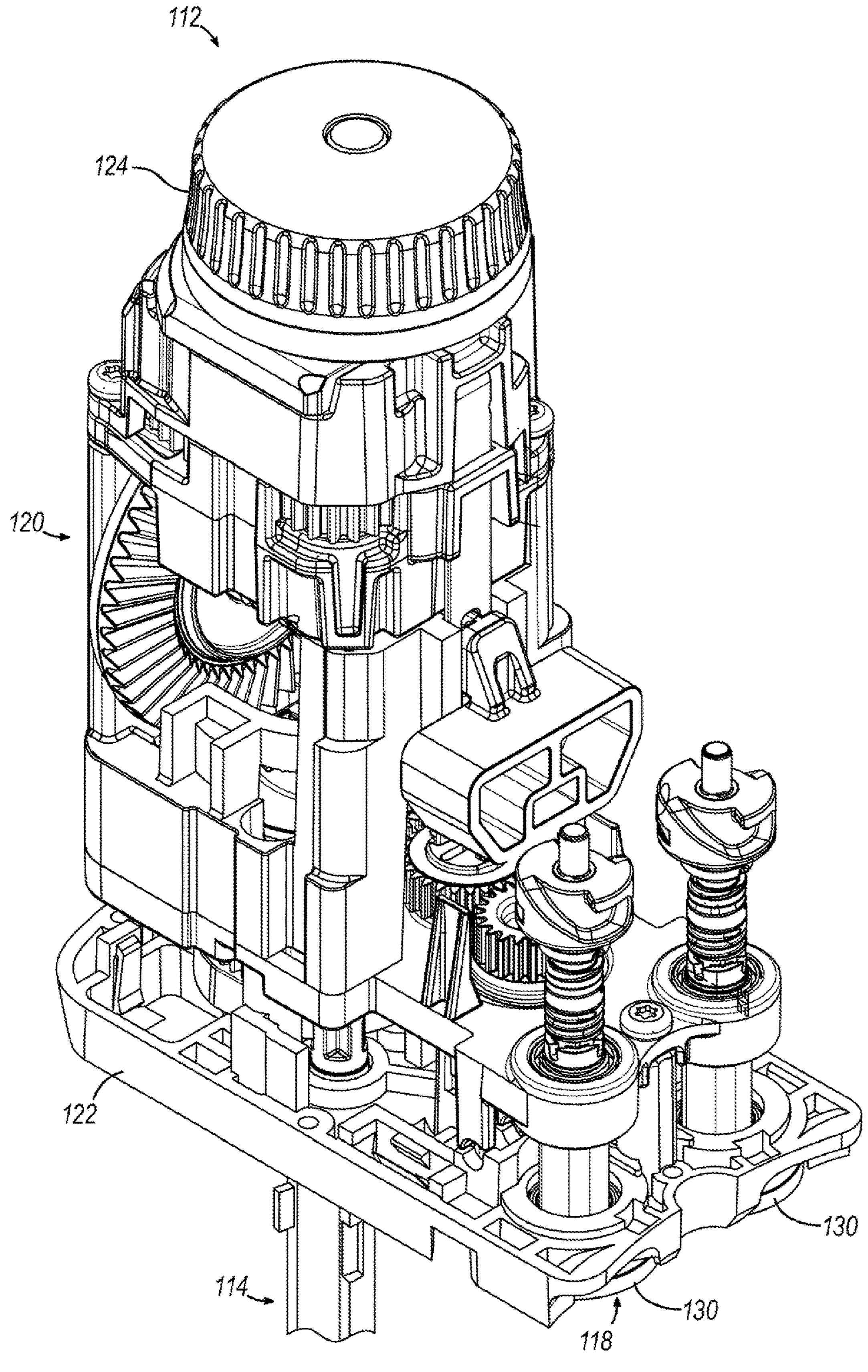
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

Figure 6:
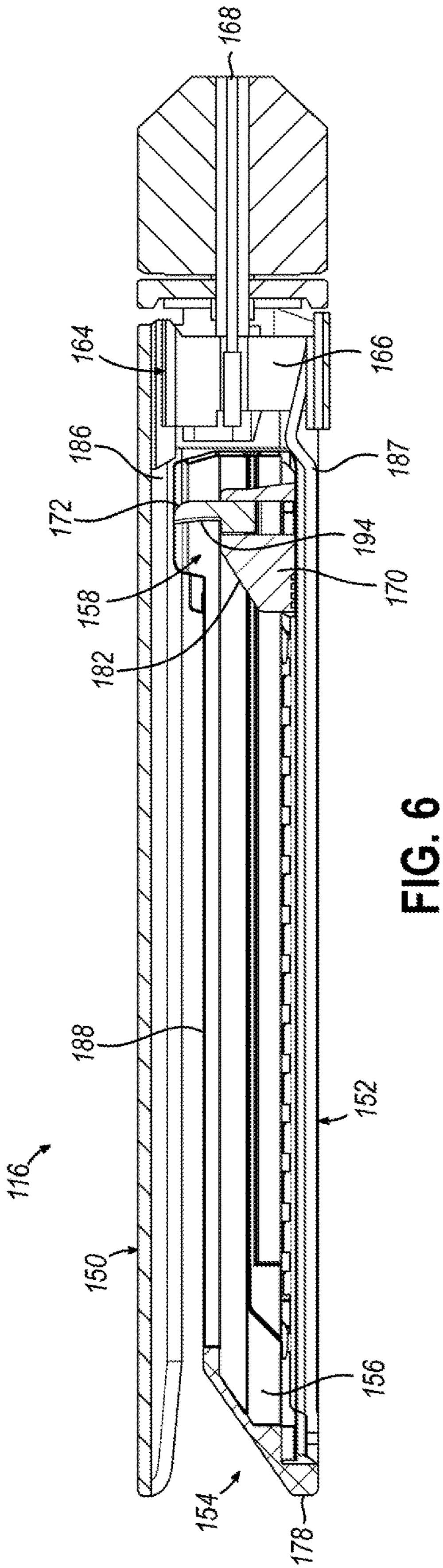
FIG. 6 depicts a side cross-sectional view of the end effector of FIG. 4, where the end effector includes a staple cartridge.

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a removable staple cartridge (154). In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
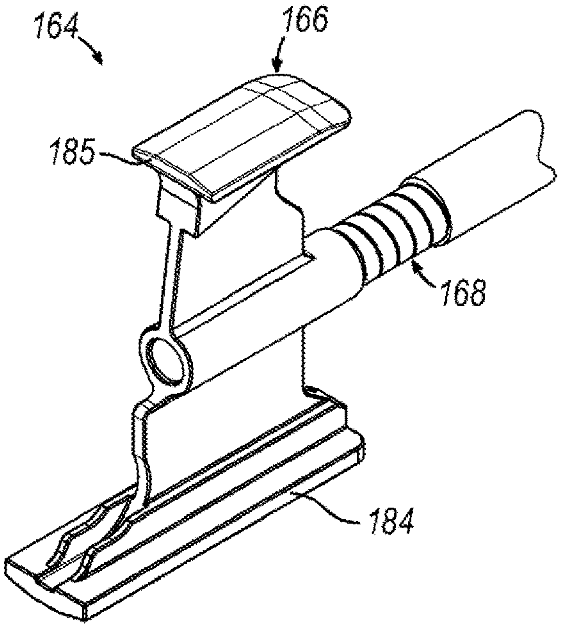
FIG. 8 depicts a driving assembly configured for use with the staple cartridge of FIG. 7.
Figure 9:
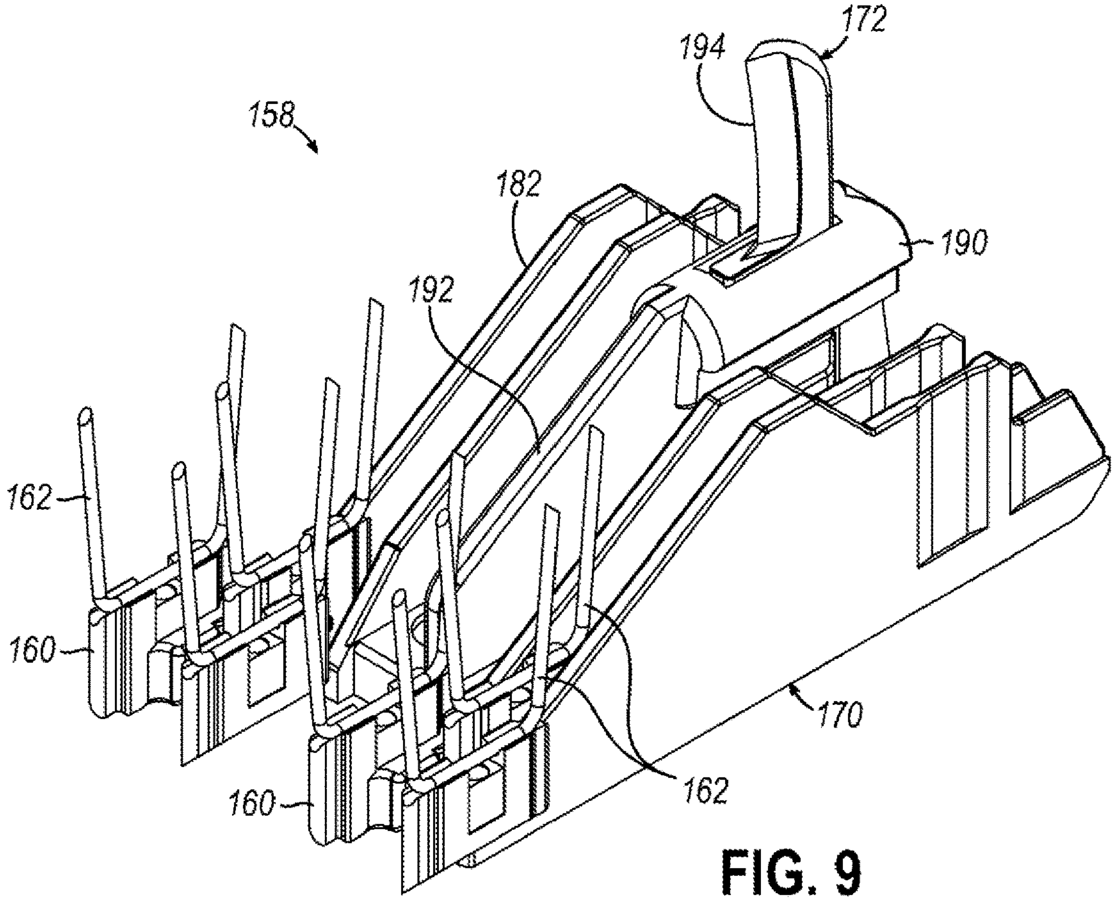
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

Figure 7:
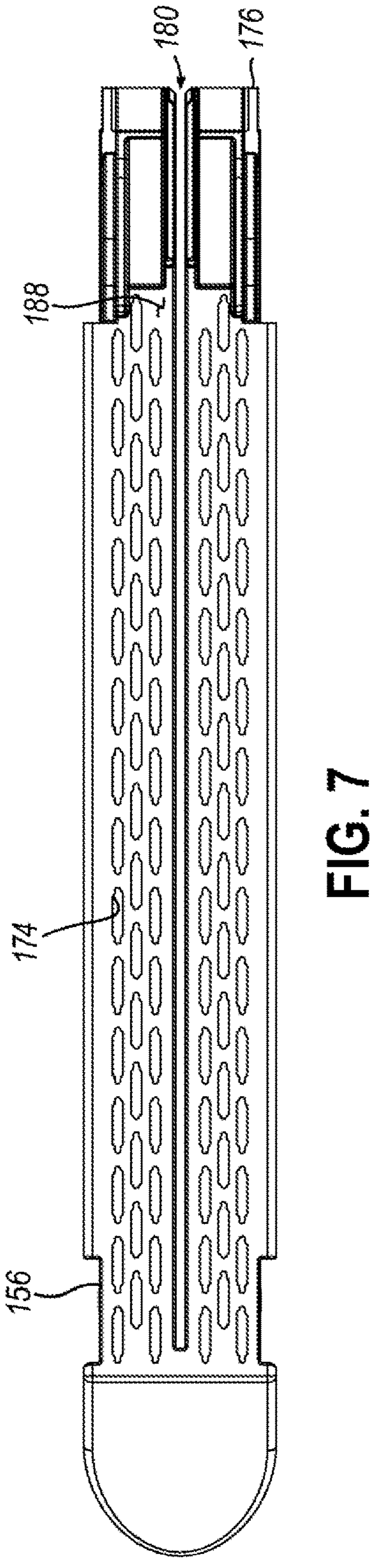
FIG. 7 depicts a top view of a deck of the staple cartridge of FIG. 6.

FIG. 7 shows a top view of staple cartridge body (156). Staple cartridge body (156) includes an array of staple accommodating apertures (174) (also known as openings) extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed; and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) laterally out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
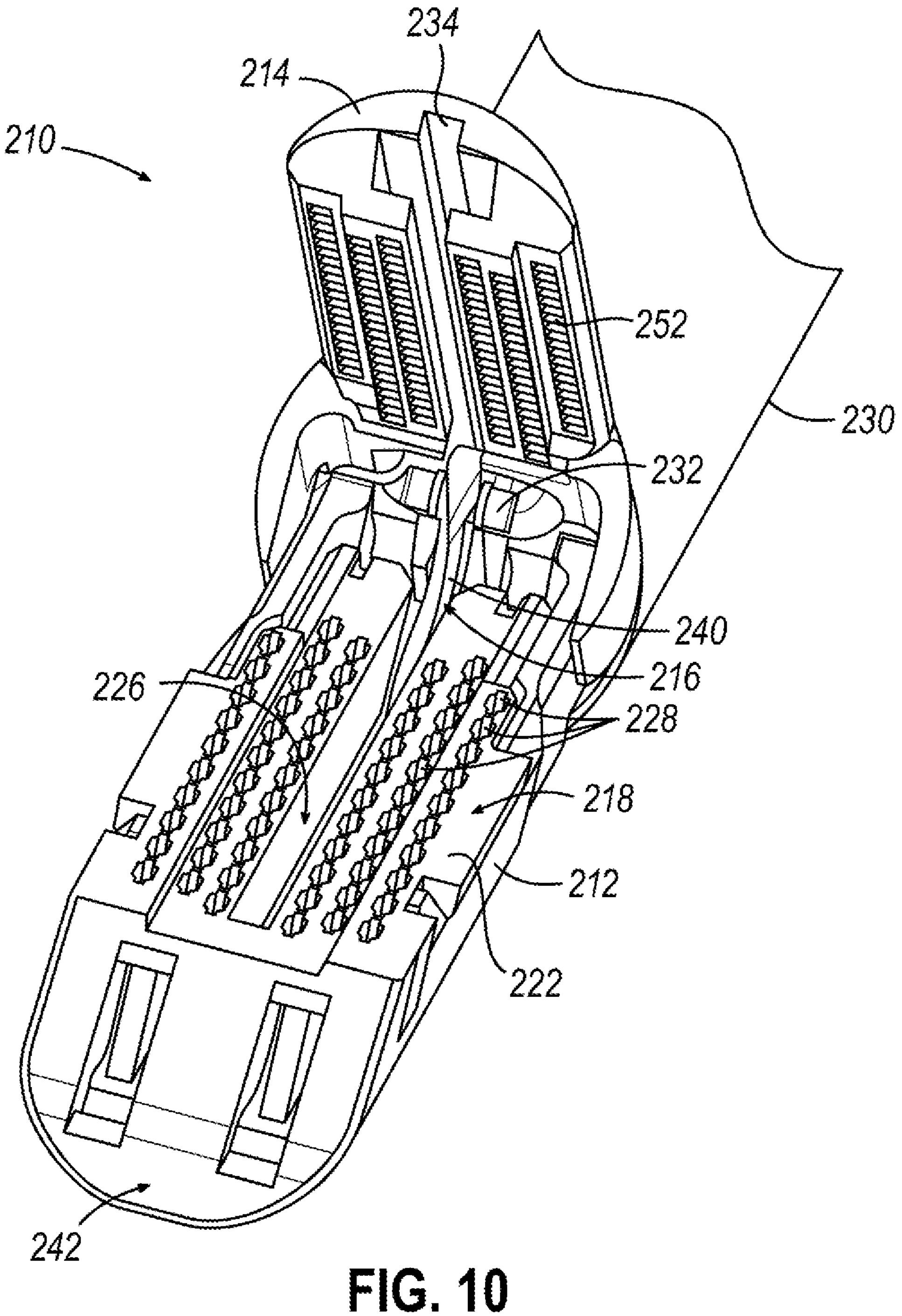
FIG. 10 depicts a second exemplary end effector that may be configured for use with the robotic surgical system of FIG. 1.
Figure 11:
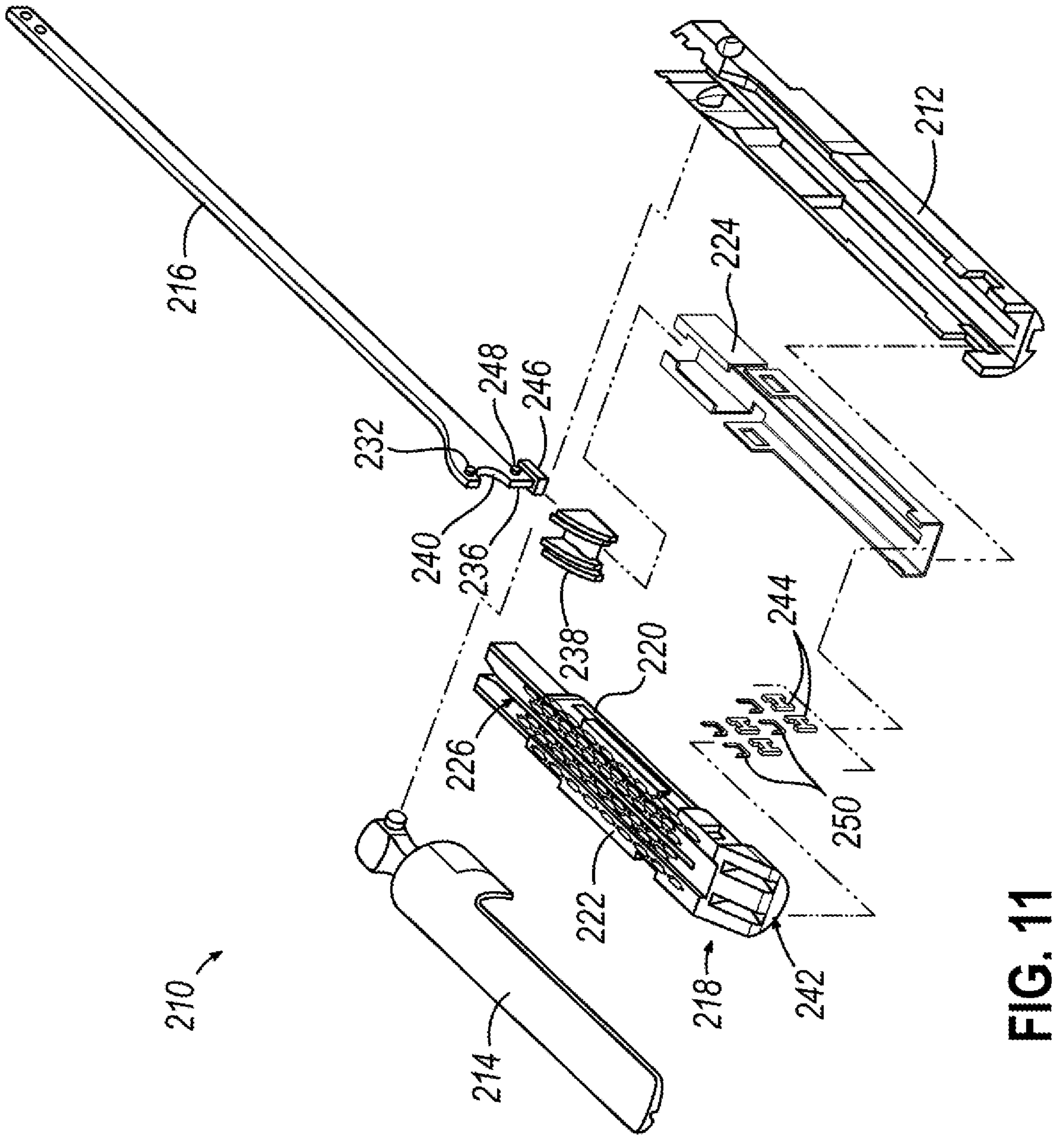
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, issued as U.S. Pat. No. 11,497,494 on Nov. 15, 2022, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, issued as U.S. Pat. No. 11,896,202 on Feb. 13, 2024, the disclosure of which is hereby incorporated by reference herein in its entirety.

It will be appreciated that any one or more of the teachings described below may be combined with any one or more of the teachings described above in connection with FIGS. 1-11.

II. Exemplary Deflectable Firing Members for Surgical Staplers

In some instances, it may be desirable to provide a firing member (e.g., a push rod) for operatively coupling pusher member (166) with moveable member (128) to transmit proximal and/or distal motion therebetween during articulation of end effector (116) relative to a longitudinal axis defined by shaft assembly (114). It may also be desirable for such a firing member to be resistant to lateral/lateral misalignment during articulation of end effector (116) (e.g., via any suitable wrist architecture of end effector (116)), to thereby prevent the firing member from buckling. Each of the push rods (310, 410, 510, 610, 710, 810, 910, 1010, 1110) described below may provide one or more of these functionalities. As used herein, the term "lateral" shall be understood to mean any direction that is laterally oriented relative to an axis; or that is otherwise non-parallel with the axis. The term "lateral" should not be read as being limited to directions that are only perpendicular to the axis. While a direction that is perpendicular to the axis may constitute a "lateral" direction, other directions that are obliquely oriented relative to the axis may also constitute "lateral" directions.

A. First Exemplary Deflectable Firing Member

FIGS. 12-14B show a distal portion of an exemplary push rod (310) for use with surgical instrument (110) described above. Push rod (310) is similar to push rod (168) described above except as otherwise described below. In this regard, push rod (310) may operatively couple a pusher member (not shown), such as pusher member (166), with an actuation mechanism (not shown), such as moveable member (128), for transmitting proximal and/or distal motion between pusher member (166) and moveable member (128).

Figure 12:
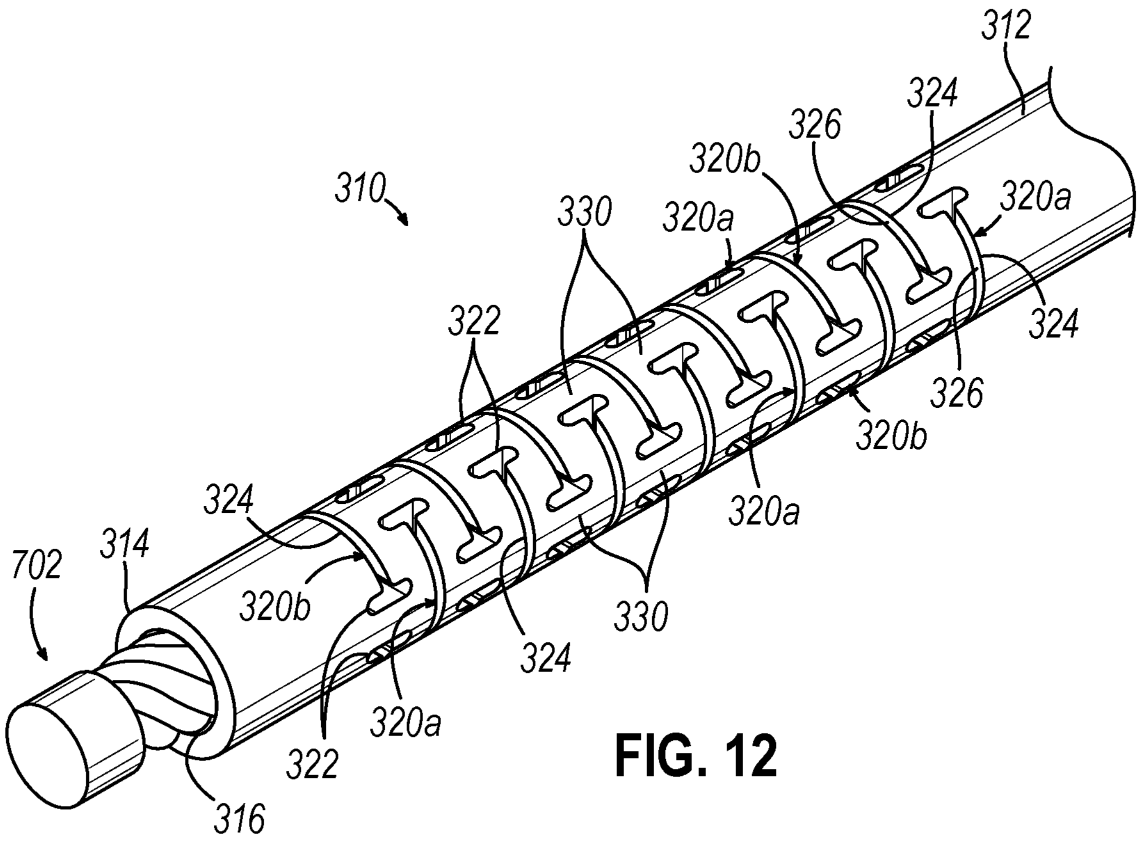
FIG. 12 depicts a perspective view of a distal portion of an exemplary push rod for use with the surgical instrument of FIG. 4.
Figure 13:
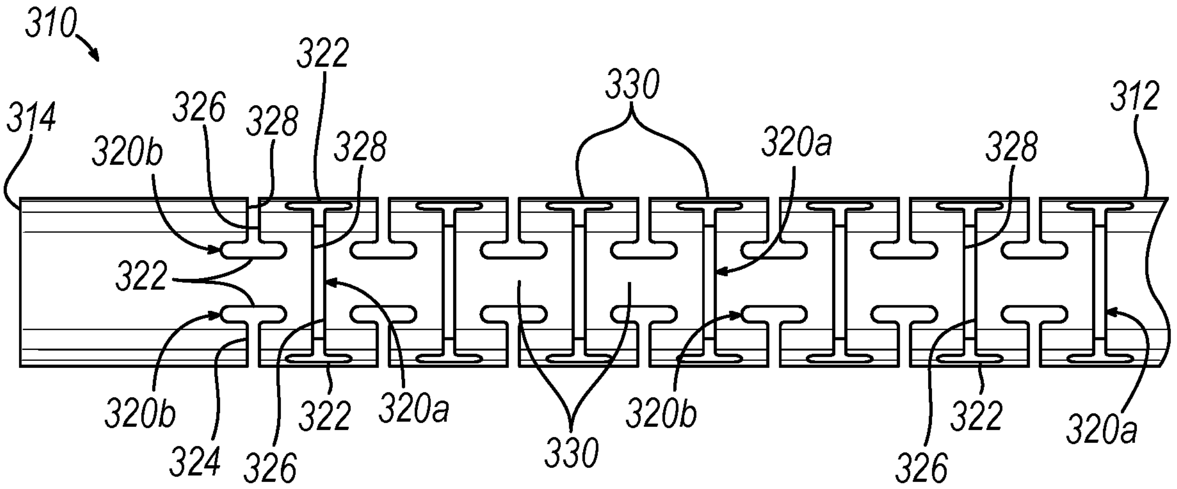
FIG. 13 depicts a side elevational view of the distal portion of the push rod of FIG. 12.

As shown in FIGS. 12-13, push rod (310) includes a cylindrical tube (312) extending distally from a proximal end (not shown) to a distal end (314) along a longitudinal axis, such as the longitudinal axis defined by shaft assembly (114). In some versions, the proximal end of cylindrical tube (312) may define an input surface for receiving forces from moveable member (128) and distal end (314) of cylindrical tube (312) may define an output surface for transmitting such forces to pusher member (166). Cylindrical tube (312) may be formed of any suitable material, such as a metal or polymer-based material. Push rod (310) also includes a lumen (316) defined by an interior surface of cylindrical tube (312). In some versions, lumen (316) may be configured to slidably receive a pull rod (702), as described below in connection with FIGS. 20-22.

Push rod (310) of the present version further includes a plurality of I-shaped slots (320*a*, 320*b*) each extending partially circumferentially about cylindrical tube (312), and each including a pair of longitudinal slot end portions (322) and an intermediate slot portion (324) extending circumferentially therebetween and having axial force transmission features in the form of longitudinally-opposed proximal and distal surfaces (326, 328). More particularly, slots (320*a*, 320*b*) are arranged in diametrically-opposed pairs spaced apart from each other at equal intervals along the length of tube (312), such that lateral alignment features in the form of a diametrically-opposed pair of bridges (330) extend circumferentially between the respective slot end portions (322) of each diametrically-opposed pair of slots (320*a*, 320*b*). In some versions, the portions of tube (312) extending longitudinally between longitudinally-adjacent pairs of slots (320*a*, 320*b*) may be referred to as "segments." As described in greater detail below, slots (320*a*, 320*b*) may impart bending flexibility to push rod (310), while bridges (330) and/or surfaces (326, 328) may impart axial stiffness and/or lateral misalignment (e.g., skew) resistance to push rod (310).

In the present version, slots (320*a*, 320*b*) are arranged in alternating pairs of diametrically-opposed slots (320*a*) and diametrically-opposed slots (320*b*), such that the pairs of diametrically-opposed slots (320*a*) are each angularly offset from the pairs of diametrically-opposed slots (320*b*), with intermediate slot portions (324) of slots (320*a*) extending circumferentially between respective laterally outer regions of tube (312), and with intermediate slot portions (324) of slots (320*b*) extending circumferentially between respective laterally outer regions of tube (312). In this manner, bridges (330) defined between the respective slot end portions (322) of each pair of diametrically-opposed slots (320*a*) are positioned at such laterally outer regions of tube (312), and bridges (330) defined between the respective slot end portions (322) of each pair of diametrically-opposed slots (320*b*) are positioned at such laterally outer regions of tube (312). In some versions, slots (320*a*, 320*b*) may each be laser cut into tube (312). It will be appreciated that slots (320*a*, 320*b*) may each be formed in any other suitable manner.

Figure 14A:
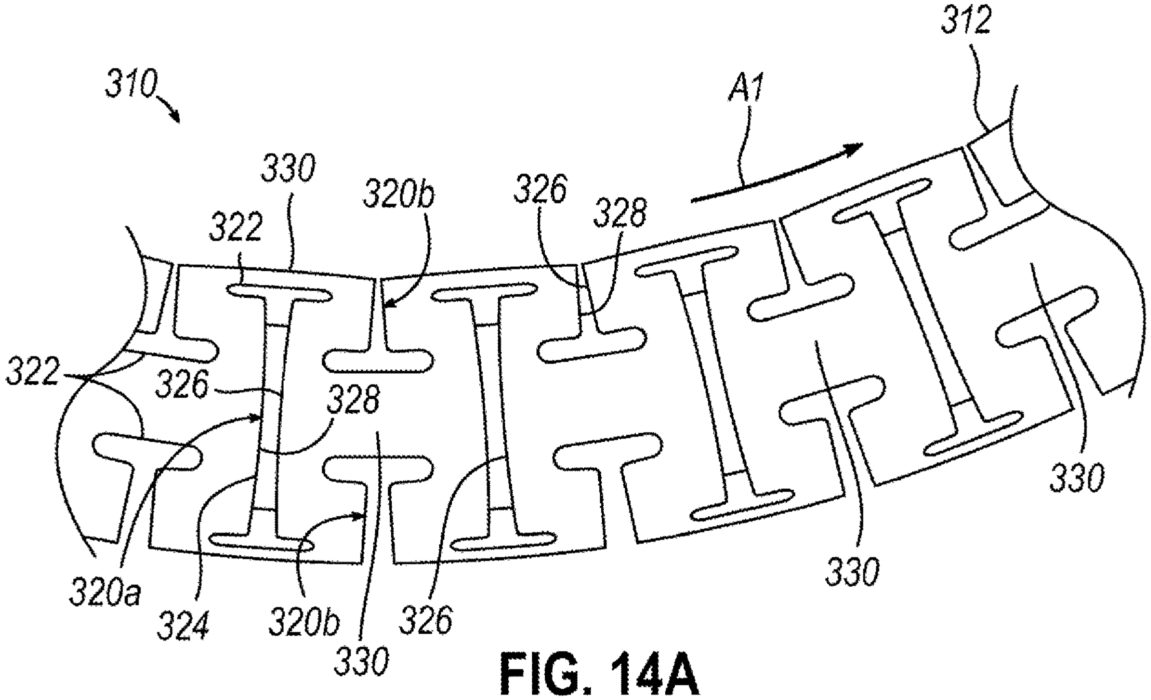
FIG. 14A depicts a side elevational view of the distal portion of the push rod of FIG. 12, showing the distal portion of the push rod in a laterally deflected state.
Figure 14B:
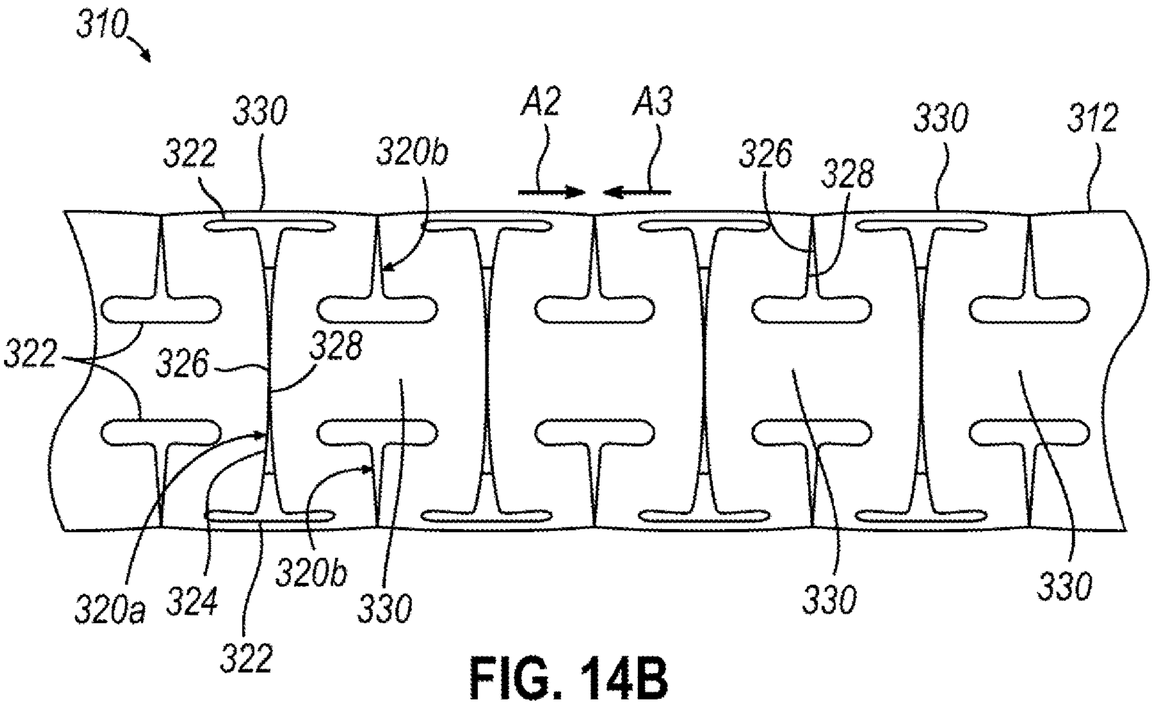
FIG. 14B depicts a side elevational view of the distal portion of the push rod of FIG. 12, showing the distal portion of the push rod in a longitudinally compressed state.

Referring now to FIGS. 14A-14B, at least a distal portion of push rod (310) is configured to transition between the natural state shown in FIGS. 12 and 13, at least one laterally deflected state (FIG. 14A), and at least one longitudinally compressed state (FIG. 14B). In some versions, push rod (310) may be resiliently biased toward the natural state, such as via bridges (330).

As shown in FIG. 14A, at least the distal portion of push rod (310) may be deflectable relative to the longitudinal axis of shaft assembly (114). In this regard, bridges (330) may be sufficiently flexible to permit the distal portion of push rod (310) to deflect laterally away from the longitudinal axis, while at least the intermediate slot portions (324) of slots (320*a*, 320*b*) may provide relief space for the longitudinally-adjacent portions of tube (312) to flex into during deflection of the distal portion, as indicated by arrow (A1) in FIG. 14A. While the distal portion of push rod (310) is shown deflecting laterally outwardly (e.g., upwardly) from the longitudinal axis, it will be appreciated that the distal portion of push rod (310) may deflect in any other lateral direction from the longitudinal axis. In this manner, push rod (310) may conform to or otherwise accommodate articulation of end effector (116) relative to the longitudinal axis defined by shaft assembly (114) (e.g., via any suitable wrist architecture of end effector (116)).

As shown in FIG. 14B, at least the distal portion of push rod (310) may also be compressible along the longitudinal axis of shaft assembly (114). In this regard, slots (320*a*, 320*b*) may permit proximal surfaces (326) to be urged into engagement with the corresponding distal surfaces (328), while bridges (330) may be sufficiently rigid to inhibit engaged pairs of proximal and distal surfaces (326, 328) from skewing or otherwise shifting away from each other in a lateral direction during application of compressive axial loads thereto, as indicated by arrows (A2, A3) in FIG. 14B. In this manner, push rod (310) may transmit compressive axial loads, such as for transmitting distal motion from moveable member (128) to pusher member (166) to advance pusher member (166) distally, via bridges (330) and/or engaged pairs of proximal and distal surfaces (326, 328), while resisting lateral misalignment of proximal and distal surfaces (326, 328) via bridges (330) to prevent push rod (310) from buckling. In other words, push rod (310) may have sufficient column strength to advance pusher member (166) distally, at least when push rod (310) is in the compressed state. In some versions, push rod (310) may also transmit tensile axial loads, such as for transmitting proximal motion from moveable member (128) to pusher member (166) to retract pusher member (166) proximally, via bridges (330).

B. Second Exemplary Deflectable Firing Member

FIGS. 15-17B show a distal portion of another exemplary push rod (410) for use with surgical instrument (110) described above. Push rod (410) is similar to push rod (168) described above except as otherwise described below. In this regard, push rod (410) may operatively couple a pusher member (not shown), such as pusher member (166), with an actuation mechanism (not shown), such as moveable member (128), for transmitting proximal and/or distal motion between pusher member (166) and moveable member (128).

Figure 15:
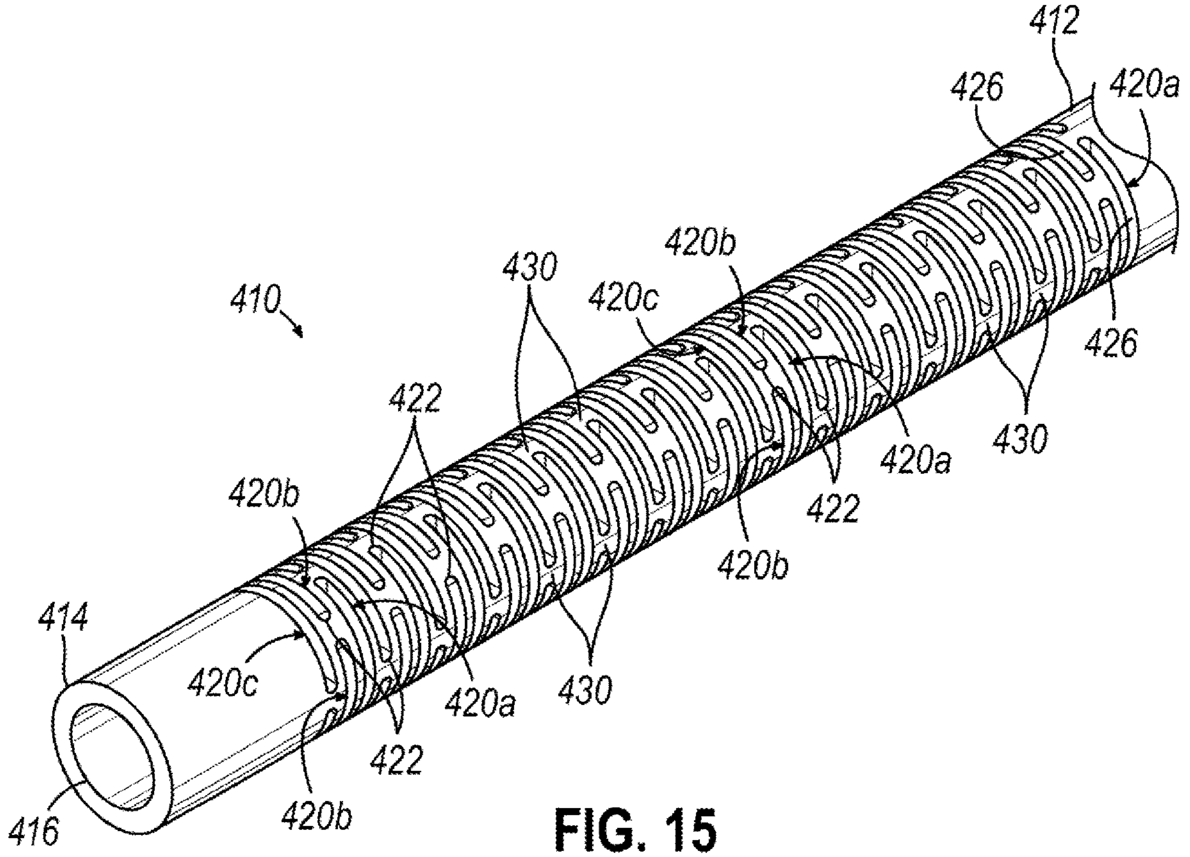
FIG. 15 depicts a perspective view of a distal portion of another exemplary push rod for use with the surgical instrument of FIG. 4.
Figure 16:
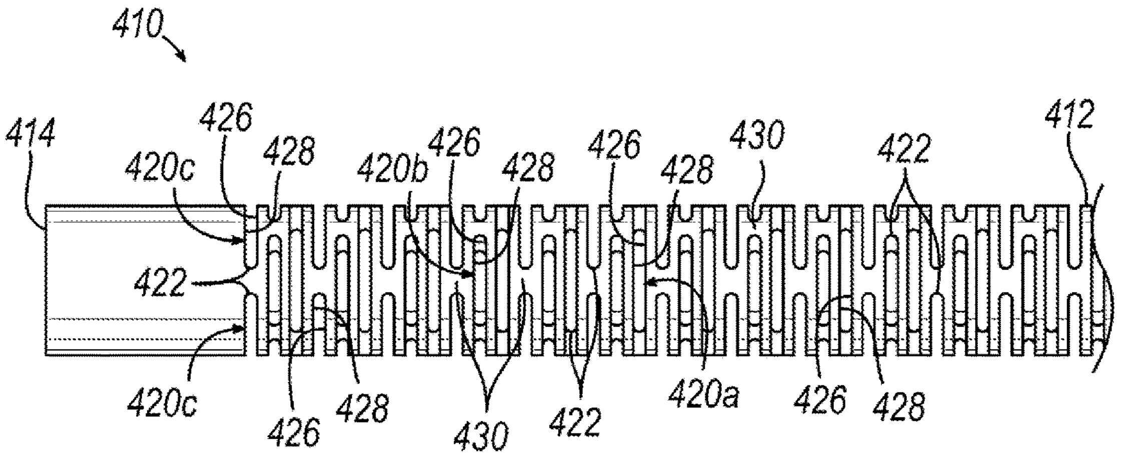
FIG. 16 depicts a side elevational view of the distal portion of the push rod of FIG. 15.

As shown in FIGS. 15-16, push rod (410) includes a cylindrical tube (412) extending distally from a proximal end (not shown) to a distal end (414) along a longitudinal axis, such as the longitudinal axis defined by shaft assembly (114). In some versions, the proximal end of cylindrical tube (412) may define an input surface for receiving forces from moveable member (128) and distal end (414) of cylindrical tube (412) may define an output surface for transmitting such forces to pusher member (166). Cylindrical tube (412) may be formed of any suitable material, such as a metal or polymer-based material. Push rod (410) also includes a lumen (416) defined by an interior surface of cylindrical tube (412). In some versions, lumen (416) may be configured to slidably receive a pull rod (not shown), as described below in connection with FIGS. 20-22.

Push rod (410) of the present version further includes a plurality of linear slots (420*a*, 420*b*, 420*c*) each extending partially circumferentially about cylindrical tube (412), and each including a pair of ends (422) and longitudinally-opposed proximal and distal surfaces (426, 428). More particularly, slots (420*a*, 420*b*, 420*c*) are arranged in diametrically-opposed pairs spaced apart from each other at equal intervals along the length of tube (412), such that a diametrically-opposed pair of bridges (430) extend circumferentially between the respective slot ends (422) of each diametrically-opposed pair of slots (420*a*, 420*b*, 420*c*). In some versions, the portions of tube (412) extending longitudinally between longitudinally-adjacent pairs of slots (420*a*, 420*b*, 420*c*) may be referred to as "segments." As described in greater detail below, slots (420*a*, 420*b*, 420*c*) may impart bending flexibility to push rod (410), while bridges (430) and/or surfaces (426, 428) may impart axial stiffness and/or lateral misalignment (e.g., skew) resistance to push rod (410).

In the present version, slots (420*a*, 420*b*, 420*c*) are arranged in alternating pairs of diametrically-opposed slots (420*a*), radially obliquely-opposed slots (420*b*), and diametrically-opposed slots (420*c*), such that the pairs of diametrically-opposed slots (420*a*) are each angularly offset from the pairs of radially obliquely-opposed slots (420*b*), and further angularly offset from the pairs of diametrically-opposed slots (420*c*), with slots (420*a*) extending circumferentially between respective laterally outer regions of tube (412), with slots (420*b*) extending circumferentially between respective radially obliquely outer regions of tube (412), and with slots (420*c*) extending circumferentially between respective laterally outer regions of tube (412). In this manner, bridges (430) defined between the respective slot ends (422) of each pair of diametrically-opposed slots (420*a*) are positioned at such laterally outer regions of tube (412), bridges (430) defined between the respective slot ends (422) of each pair of radially obliquely-opposed slots (420*b*) are positioned at such radially obliquely outer regions of tube (412), and bridges (430) defined between the respective slot ends (422) of each pair of diametrically-opposed slots (420*c*) are positioned at such laterally outer regions of tube (412). In some versions, slots (420*a*, 420*b*, 420*c*) may each be laser cut into tube (412). It will be appreciated that slots (420*a*, 420*b*, 420*c*) may each be formed in any other suitable manner.

Figure 17A:
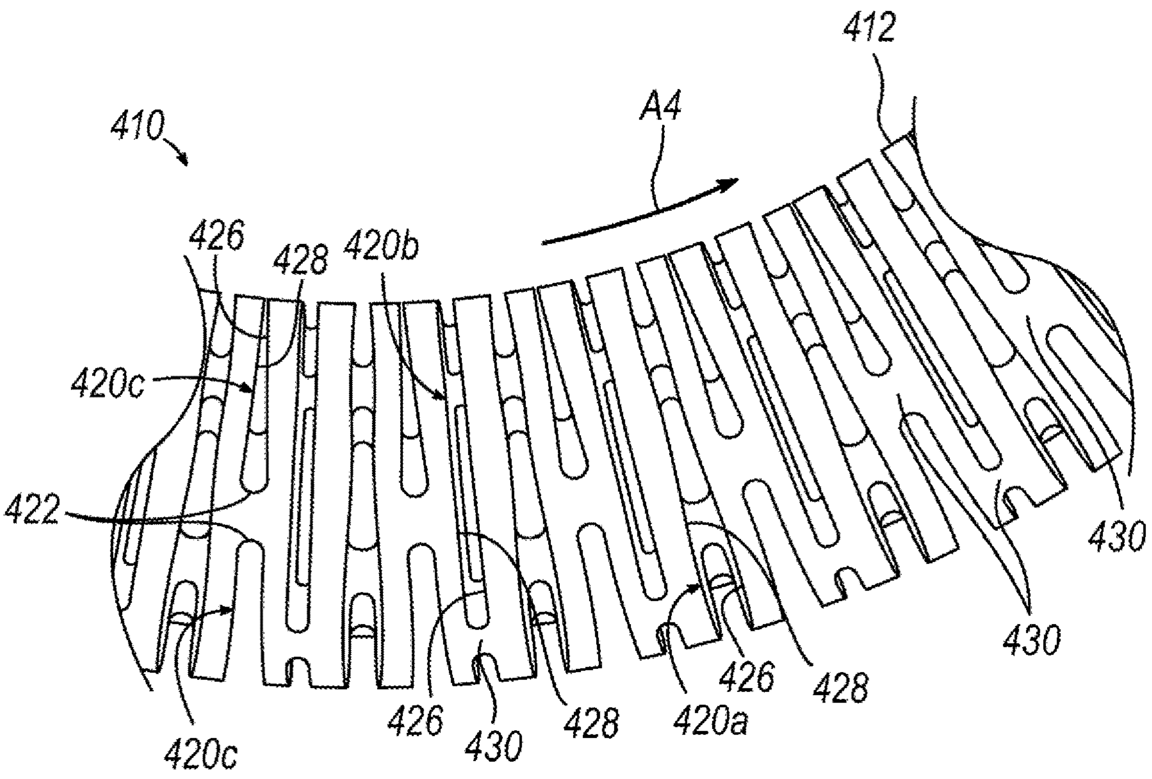
FIG. 17A depicts a side elevational view of the distal portion of the push rod of FIG. 15, showing the distal portion of the push rod in a laterally deflected state.
Figure 17B:
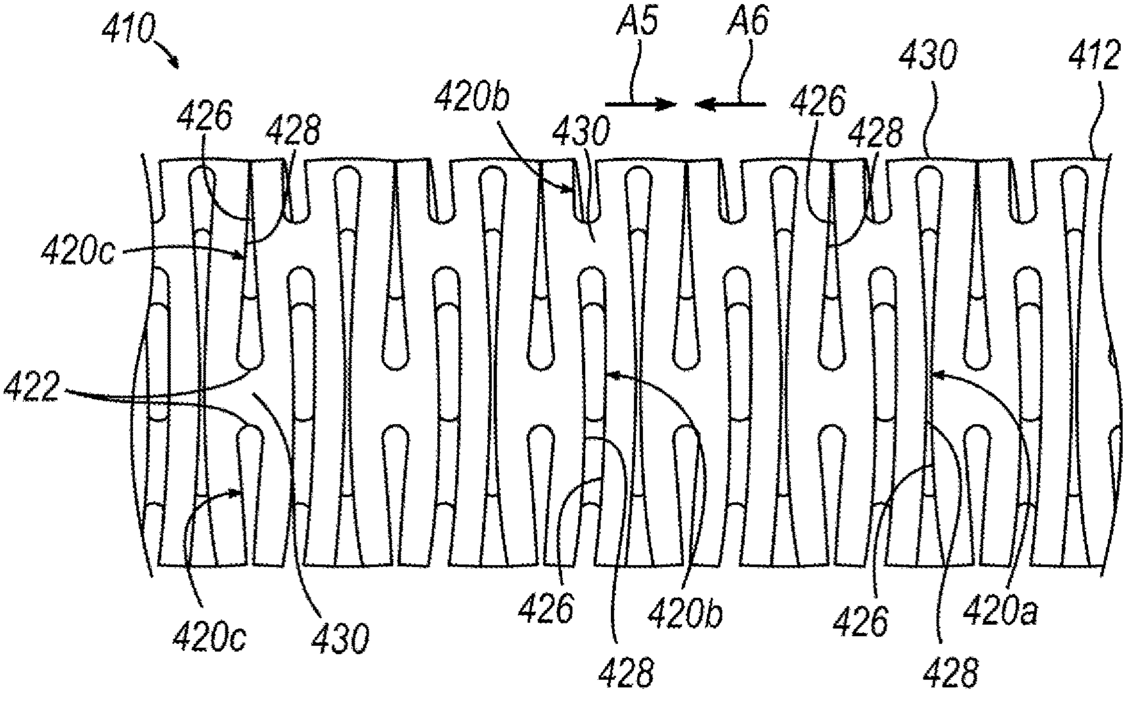
FIG. 17B depicts a side elevational view of the distal portion of the push rod of FIG. 15, showing the distal portion of the push rod in a longitudinally compressed state.

Referring now to FIGS. 17A-17B, at least a distal portion of push rod (410) is configured to transition between the natural state shown in FIGS. 15 and 16, at least one laterally deflected state (FIG. 17A), and at least one longitudinally compressed state (FIG. 17B). In some versions, push rod (410) may be resiliently biased toward the natural state, such as via bridges (430).

As shown in FIG. 17A, at least the distal portion of push rod (410) may be deflectable relative to the longitudinal axis of shaft assembly (114). In this regard, bridges (430) may be sufficiently flexible to permit the distal portion of push rod (410) to deflect laterally away from the longitudinal axis, while slots (420*a*, 420*b*, 420*c*) may provide relief space for the longitudinally-adjacent portions of tube (412) to flex into during deflection of the distal portion, as indicated by arrow (A4) in FIG. 17A. While the distal portion of push rod (410) is shown deflecting laterally outwardly (e.g., upwardly) from the longitudinal axis, it will be appreciated that the distal portion of push rod (410) may deflect outwardly in any other lateral direction from the longitudinal axis. In this manner, push rod (410) may conform to or otherwise accommodate articulation of end effector (116) relative to the longitudinal axis defined by shaft assembly (114) (e.g., via any suitable wrist architecture of end effector (116)).

As shown in FIG. 17B, at least the distal portion of push rod (410) may also be compressible along the longitudinal axis of shaft assembly (114). In this regard, slots (420*a*, 420*b*, 420*c*) may permit proximal surfaces (426) to be urged into engagement with the corresponding distal surfaces (428), while bridges (430) may be sufficiently rigid to inhibit engaged pairs of proximal and distal surfaces (426, 428) from skewing or otherwise shifting away from each other in a lateral direction during application of compressive axial loads thereto, as indicated by arrows (A5, A6) in FIG. 17B. In this manner, push rod (410) may transmit compressive axial loads, such as for transmitting distal motion from moveable member (128) to pusher member (166) to advance pusher member (166) distally, via bridges (430) and/or engaged pairs of proximal and distal surfaces (426, 428), while resisting lateral misalignment of proximal and distal surfaces (426, 428) via bridges (430) to prevent push rod (410) from budding. In other words, push rod (410) may have sufficient column strength to advance pusher member (166) distally, at least when push rod (410) is in the compressed state. In some versions, push rod (410) may also transmit tensile axial loads, such as for transmitting proximal motion from moveable member (128) to pusher member (166) to retract pusher member (166) proximally, via bridges (430).

C. Third Exemplary Deflectable Firing Member

Figure 18:
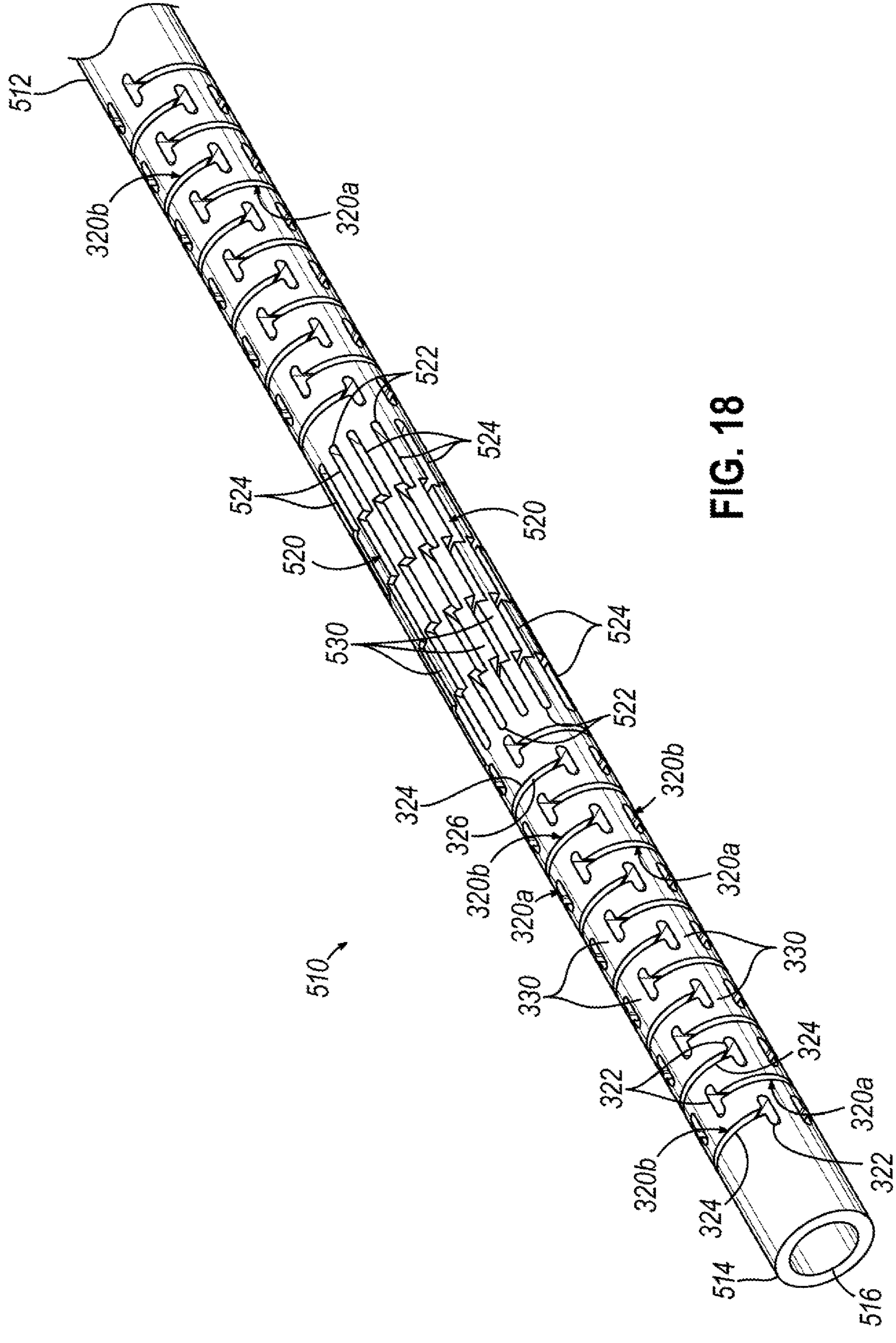
FIG. 18 depicts a perspective view of a distal portion of another exemplary push rod for use with the surgical instrument of FIG. 4.

FIG. 18 shows a distal portion of another exemplary push rod (510) for use with surgical instrument (110) described above. Push rod (510) is similar to push rod (168) described above except as otherwise described below. In this regard, push rod (510) may operatively couple a pusher member (not shown), such as pusher member (166), with an actuation mechanism (not shown), such as moveable member (128), for transmitting proximal and/or distal motion between pusher member (166) and moveable member (128).

As shown, push rod (510) includes a cylindrical tube (512) extending distally from a proximal end (not shown) to a distal end (514) along a longitudinal axis, such as the longitudinal axis defined by shaft assembly (114). In some versions, the proximal end of cylindrical tube (512) may define an input surface for receiving forces from moveable member (128) and distal end (514) of cylindrical tube (512) may define an output surface for transmitting such forces to pusher member (166). Cylindrical tube (512) may be formed of any suitable material, such as a metal or polymer-based material. Push rod (510) also includes a lumen (516) defined by an interior surface of cylindrical tube (512). In some versions, lumen (516) may be configured to slidably receive a pull rod (not shown), as described below in connection with FIGS. 20-22.

Push rod (510) of the present version further includes a plurality of I-shaped slots (320*a*, 320*b*) defining corresponding bridges (330). Push rod (510) further includes a plurality of step-shaped slots (520) each extending partially longitudinally along cylindrical tube (512), and each including a pair of slot ends (522) and a plurality of linear slot portions (524) extending longitudinally therebetween and angularly offset from each other. More particularly, slots (520) are spaced apart from each other at equal intervals about the circumference of tube (512), such that a step-shaped bridge (530) extends circumferentially between each circumferentially-adjacent pair of slots (520). In some versions, the portions of tube (512) extending longitudinally between longitudinally-adjacent pairs of slots (320*a*, 320*b*) may be referred to as "segments." As described in greater detail below, slots (320*a*, 320*b*, 520) may impart bending flexibility to push rod (510), while bridges (330, 530) and/or surfaces (326, 328) may impart axial stiffness and/or lateral misalignment (e.g., skew) resistance to push rod (510).

In the present version, slots (320*a*, 320*b*) are arranged in a manner similar to that described above in connection with FIGS. 12-14B, and are further divided into proximal and distal sets, with slots (520) interposed between the proximal set of slots (320*a*, 320*b*) and the distal set of slots (320*a*, 320*b*). In some versions, slots (320*a*, 320*b*, 520) may each be laser cut into tube (512). It will be appreciated that slots (320*a*, 320*b*, 520) may each be formed in any other suitable manner.

It will be appreciated that at least a distal portion of push rod (510) is configured to transition between the natural state shown in FIG. 18, at least one laterally deflected state (not shown), and at least one longitudinally compressed state (not shown), in manners similar to those described above in connection with FIGS. 14A-14B and 17A-17B. In some versions, push rod (510) may be resiliently biased toward the natural state, such as via bridges (330, 530).

For example, at least the distal portion of push rod (510) may be deflectable relative to the longitudinal axis of shaft assembly (114). In this regard, bridges (330, 530) may be sufficiently flexible to permit the distal portion of push rod (510) to deflect laterally outwardly from the longitudinal axis, while slots (320*a*, 320*b*, 520) may provide relief space for the longitudinally-adjacent and/or circumferentially-adjacent portions of tube (512) to flex into during deflection of the distal portion. In this manner, push rod (510) may conform to or otherwise accommodate articulation of end effector (116) relative to the longitudinal axis defined by shaft assembly (114) (e.g., via any suitable wrist architecture of end effector (116)).

At least the distal portion of push rod (510) may also be compressible along the longitudinal axis of shaft assembly (114). In this regard, slots (320*a*, 320*b*) may permit proximal surfaces (326) to be urged into engagement with the corresponding distal surfaces (328), while bridges (330) may be sufficiently rigid to inhibit engaged pairs of proximal and distal surfaces (326, 328) from skewing or otherwise shifting away from each other in a lateral direction during application of compressive axial loads thereto. In this manner, push rod (510) may transmit compressive axial loads, such as for transmitting distal motion from moveable member (128) to pusher member (166) to advance pusher member (166) distally, via bridges (330, 530) and/or engaged pairs of proximal and distal surfaces (326, 328), while resisting lateral misalignment of proximal and distal surfaces (326, 328) via bridges (330) to prevent push rod (510) from buckling. In other words, push rod (510) may have sufficient column strength to advance pusher member (166) distally, at least when push rod (510) is in the compressed state. In some versions, push rod (510) may also transmit tensile axial loads, such as for transmitting proximal motion from moveable member (128) to pusher member (166) to retract pusher member (166) proximally, via bridges (330, 530).

D. Fourth Exemplary Deflectable Firing Member

Figure 19:
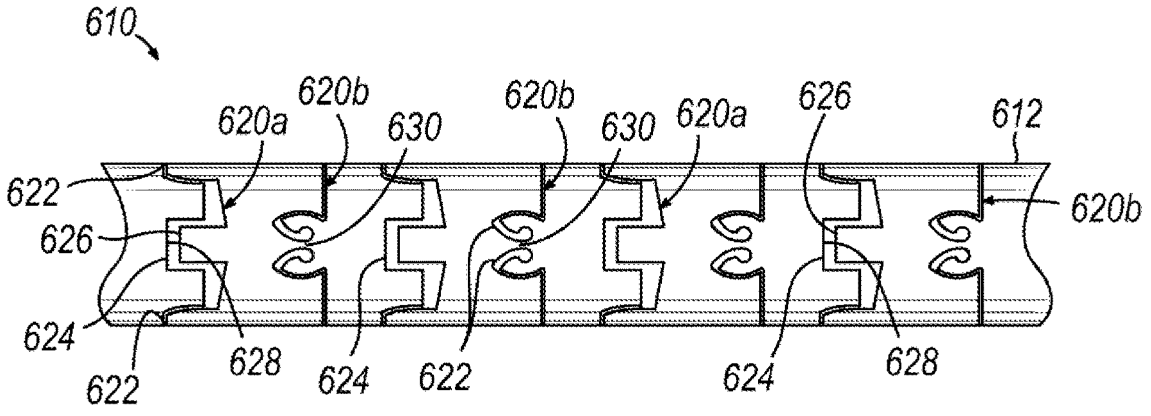
FIG. 19 depicts a side elevational view of a distal portion of another exemplary push rod for use with the surgical instrument of FIG. 4.

FIG. 19 shows a distal portion of another exemplary push rod (610) for use with surgical instrument (110) described above. Push rod (610) is similar to push rod (168) described above except as otherwise described below. In this regard, push rod (610) may operatively couple a pusher member (not shown), such as pusher member (166), with an actuation mechanism (not shown), such as moveable member (128), for transmitting proximal and/or distal motion between pusher member (166) and moveable member (128).

As shown, push rod (610) includes a cylindrical tube (612) extending distally from a proximal end (not shown) to a distal end (not shown) along a longitudinal axis, such as the longitudinal axis defined by shaft assembly (114). In some versions, the proximal end of cylindrical tube (612) may define an input surface for receiving forces from moveable member (128) and the distal end of cylindrical tube (612) may define an output surface for transmitting such forces to pusher member (166). Cylindrical tube (612) may be formed of any suitable material, such as a metal or polymer-based material. Push rod (610) may also include a lumen (not shown) defined by an interior surface of cylindrical tube (612). In some versions, the lumen may be configured to slidably receive a pull rod (not shown), as described below in connection with FIGS. 20-22.

Push rod (610) of the present version further includes a plurality of slots (620*a*, 620*b*) each extending partially circumferentially about cylindrical tube (612), and each including a pair of generally hook-shaped slot end portions (622) and a generally U-shaped intermediate slot portion (624) extending circumferentially therebetween and having longitudinally-opposed proximal and distal surfaces (626, 628). More particularly, slots (620*a*, 620*b*) are arranged in diametrically-opposed pairs spaced apart from each other at equal intervals along the length of tube (612), such that a diametrically-opposed pair of bridges (630) extend circumferentially between the respective slot end portions (622) of each diametrically-opposed pair of slots (620*a*, 620*b*). In some versions, the portions of tube (612) extending longitudinally between longitudinally-adjacent pairs of slots (620*a*, 620*b*) may be referred to as "segments." As described in greater detail below, slots (620*a*, 620*b*) may impart bending flexibility to push rod (610), while bridges (630) and/or surfaces (626, 628) may impart axial stiffness and/or lateral misalignment (e.g., skew) resistance to push rod (610).

In the present version, slots (620*a*, 620*b*) are arranged in alternating pairs of diametrically-opposed slots (620*a*) and diametrically-opposed slots (620*b*), such that the pairs of diametrically-opposed slots (620*a*) are each angularly offset from the pairs of diametrically-opposed slots (620*b*), with intermediate slot portions (624) of slots (620*a*) extending circumferentially between respective laterally outer regions of tube (612), and with intermediate slot portions (624) of slots (620*b*) extending circumferentially between respective laterally outer regions of tube (612). In this manner, bridges (630) defined between the respective slot end portions (622) of each pair of diametrically-opposed slots (620*a*) are positioned at such laterally outer regions of tube (612), and bridges (630) defined between the respective slot end portions (622) of each pair of diametrically-opposed slots (620*b*) are positioned at such laterally outer regions of tube (612). In some versions, slots (620*a*, 620*b*) may each be laser cut into tube (612). It will be appreciated that slots (620*a*, 620*b*) may each be formed in any other suitable manner.

It will be appreciated that at least a distal portion of push rod (610) is configured to transition between the natural state shown in FIG. 19, at least one laterally deflected state (not shown), and at least one longitudinally compressed state (not shown), in manners similar to those described above in connection with FIGS. 14A-14B and 17A-17B. In some versions, push rod (610) may be resiliently biased toward the natural state, such as via bridges (630).

For example, at least the distal portion of push rod (610) may be deflectable relative to the longitudinal axis of shaft assembly (114). In this regard, bridges (630) may be sufficiently flexible to permit the distal portion of push rod (610) to deflect laterally away from the longitudinal axis, while slots (620*a*, 620*b*) may provide relief space for the longitudinally-adjacent portions of tube (612) to flex into during deflection of the distal portion. In this manner, push rod (610) may conform to or otherwise accommodate articulation of end effector (116) relative to the longitudinal axis defined by shaft assembly (114) (e.g., via any suitable wrist architecture of end effector (116)).

At least the distal portion of push rod (610) may also be compressible along the longitudinal axis of shaft assembly (114). In this regard, slots (620*a*, 620*b*) may permit proximal surfaces (626) to be urged into engagement with the corresponding distal surfaces (628), while bridges (630) may be sufficiently rigid to inhibit engaged pairs of proximal and distal surfaces (626, 628) from skewing or otherwise shifting away from each other in a lateral direction during application of compressive axial loads thereto. In this manner, push rod (610) may transmit compressive axial loads, such as for transmitting distal motion from moveable member (128) to pusher member (166) to advance pusher member (166) distally, via bridges (630) and/or engaged pairs of proximal and distal surfaces (626, 628), while resisting lateral misalignment of proximal and distal surfaces (626, 628) via bridges (630) to prevent push rod (610) from buckling. In other words, push rod (610) may have sufficient column strength to advance pusher member (166) distally, at least when push rod (610) is in the compressed state. In some versions, push rod (610) may also transmit tensile axial loads, such as for transmitting proximal motion from moveable member (128) to pusher member (166) to retract pusher member (166) proximally, via bridges (630).

E. Fifth Exemplary Deflectable Firing Member

Figure 20:
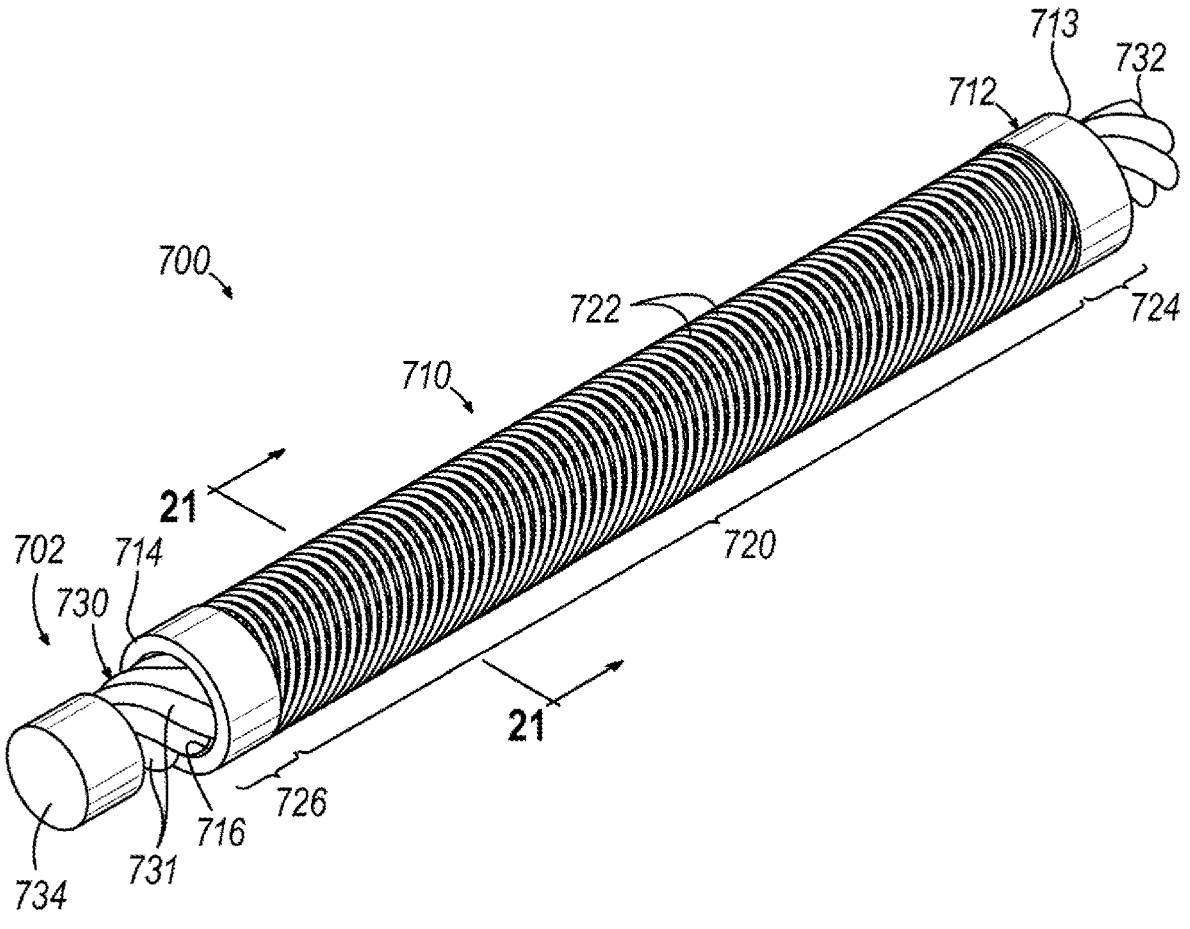
FIG. 20 depicts a perspective view of a distal portion of an exemplary actuation assembly, including an exemplary pull rod and another exemplary push rod for use with the surgical instrument of FIG. 4.
Figure 21:
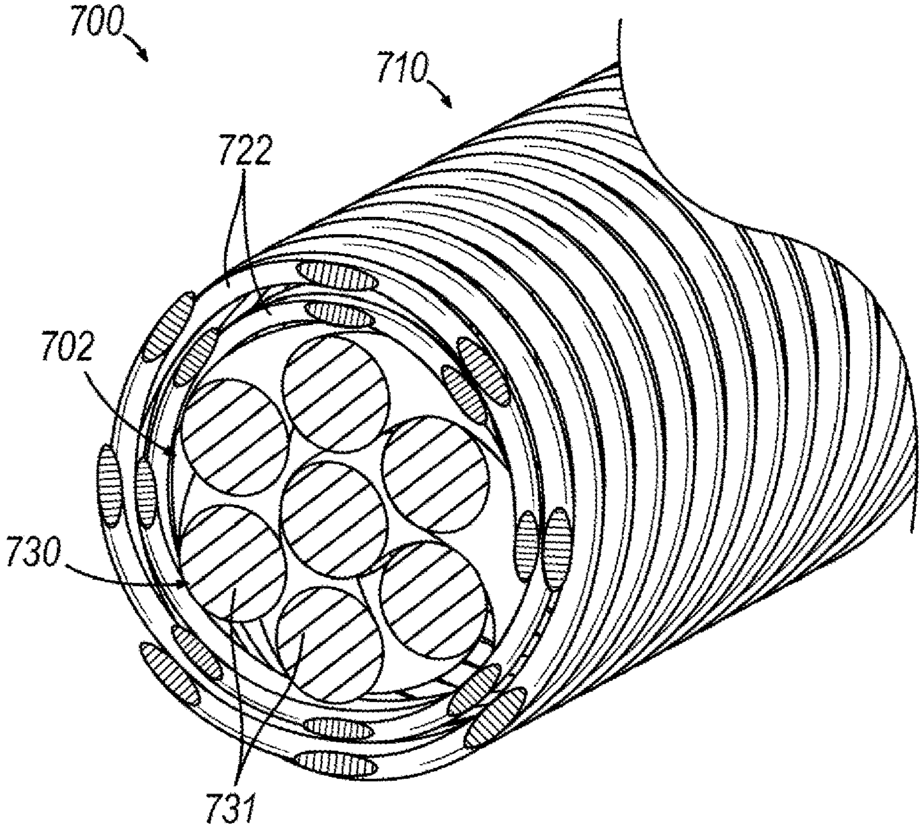
FIG. 21 depicts a cross-sectional view of the distal portion of the actuation assembly of FIG. 20, taken along section line 21-21 in FIG. 20.
Figure 22:
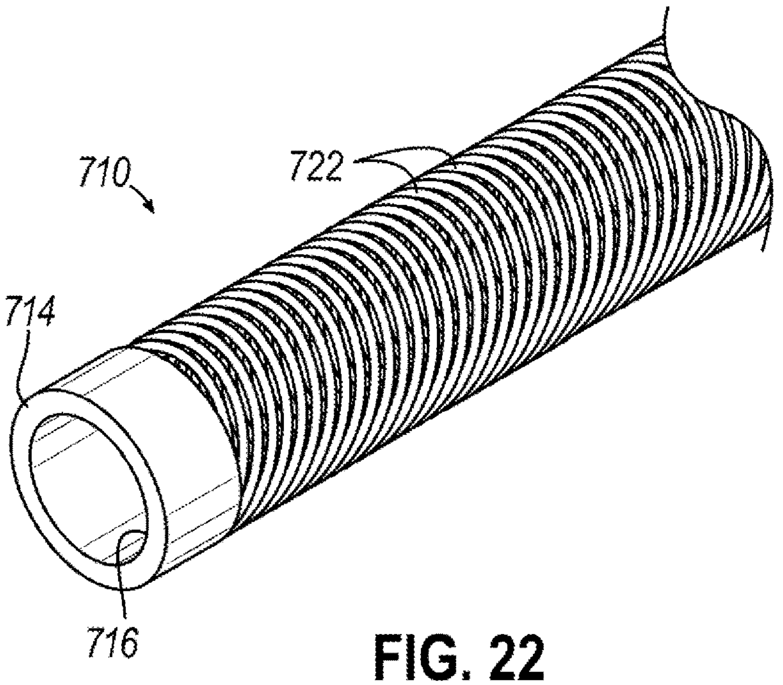
FIG. 22 depicts a perspective view of a distal portion of the push rod of FIG. 20.

FIGS. 20-22 show an actuation assembly (700) including a pull rod (702) and another exemplary push rod (710) for use with surgical instrument (110) described above. Push rod (710) is similar to push rod (168) described above except as otherwise described below. In this regard, push rod (710) may operatively couple a pusher member (not shown), such as pusher member (166), with an actuation mechanism (not shown), such as moveable member (128), for transmitting distal motion between pusher member (166) and moveable member (128). Likewise, pull rod (702) may operatively couple pusher member (166) with another actuation mechanism (not shown) for transmitting proximal motion between pusher member (166) and such another actuation mechanism.

As shown, push rod (710) includes a cylindrical tube (712) extending distally from a proximal end (713) to a distal end (714) along a longitudinal axis, such as the longitudinal axis defined by shaft assembly (114). In some versions, proximal end (713) of cylindrical tube (712) may define an input surface for receiving forces from moveable member (128) and distal end (714) of cylindrical tube (712) may define an output surface for transmitting such forces to pusher member (166). Cylindrical tube (712) may be formed of any suitable material, such as a metal or polymer-based material. Push rod (710) also includes a lumen (716) defined by an interior surface of cylindrical tube (712) for slidably receiving pull rod (702).

Cylindrical tube (712) of the present version further includes an intermediate flexible mesh portion (720) having a plurality of strands (722) that are combined in a matrix extending between proximal and distal rigid collar portions (724, 726) of cylindrical tube (712). In some versions, intermediate mesh portion (720) may have a smaller inner diameter than that of one or both collar portion(s) (724, 726). Intermediate mesh portion (720) may have any suitable configuration, such as a webbed and/or coiled configuration. In some versions, strands (722) may be 3D printed together to form intermediate mesh portion (720). In other versions, strands (722) may be individually formed as separate wires and knitted or woven together in a pattern or in a random association. Any number of suitable texture patterns may be used as would be apparent to a person having ordinary skill in the art in view of the teachings herein. Lasering and/or soldering techniques may be used to impart strands (722) and/or intermediate mesh portion (720) with a variety of different mechanical properties. It will be appreciated that strands (722) and/or intermediate mesh portion (720) may each be formed in any other suitable manner. As described in greater detail below, intermediate mesh portion (720) including strands (722) may impart bending flexibility and/or axial stiffness to push rod (710).

As shown, pull rod (702) includes a shaft in the form of a braided cable (730) including a plurality of strands (731) and extending distally from a proximal end (732) to a distal aglet (734) along a longitudinal axis, such as the longitudinal axis defined by shaft assembly (114). As described in greater detail below, braided cable (730) may impart axial stiffness and/or lateral misalignment (e.g., skew) resistance to pull rod (702), which may in turn impart lateral misalignment (e.g., skew) resistance to push rod (710) via contact between an outer surface of pull rod (702) and lumen (716). In this regard, braided cable (730) may have a stiffness greater than that of intermediate mesh portion (720) and may have an outer diameter substantially equal to or slightly less than the inner diameter of at least intermediate mesh portion (720) of push rod (710) such that pull rod (702) may be slidable longitudinally relative to push rod (710) while providing radial support thereto. Braided cable (730) may be formed of any suitable material, such as high strength steel. It will be appreciated that the shaft of pull rod (702) may be provided in any other suitable form, such as a 3D printed and/or flexible rod.

It will be appreciated that push rod (710) is configured to transition between the natural state shown in FIGS. 20-22, at least one laterally deflected state (not shown), and at least one longitudinally compressed state (not shown), in manners similar to those described above in connection with FIGS. 14A-14B and 17A-17B. Pull rod (702) is also configured to transition between the natural state shown in FIGS. 20-21 and at least one laterally deflected state (not shown). In some versions, pull rod (702) may be resiliently biased toward its natural state, such as via braided cable (730), and push rod (710) may likewise be resiliently biased toward its natural state, such as via strands (722) and/or via the resilient biasing of pull rod (702) toward its natural state.

For example, push rod (710) and pull rod (702) may each be deflectable relative to the longitudinal axis of shaft assembly (114). In this regard, strands (722) may be sufficiently flexible to permit the distal portion of push rod (710) to deflect laterally away from the longitudinal axis, while braided cable (730) may be sufficiently flexible to permit the distal portion of pull rod (702) to deflect laterally away from the longitudinal axis, such that push rod (710) and pull rod (702) may deflect laterally together. In this manner, push rod (710) and pull rod (702) may cooperatively conform to or otherwise accommodate articulation of end effector (116) relative to the longitudinal axis defined by shaft assembly (114) (e.g., via any suitable wrist architecture of end effector (116)).

At least the distal portion of push rod (710) may also be compressible along the longitudinal axis of shaft assembly (114). In this regard, strands (722) may be sufficiently flexible in the longitudinal direction to permit longitudinally-adjacent strands (722) to be urged into engagement with each other, while braided cable (730) may be sufficiently rigid in each radial direction to inhibit engaged pairs of strands (722) from skewing or otherwise shifting away from each other in a radial direction during application of compressive axial loads thereto. In this manner, push rod (710) may transmit compressive axial loads, such as for transmitting distal motion from moveable member (128) to pusher member (166) to advance pusher member (166) distally, via engaged pairs of strands (722), while resisting lateral misalignment of strands (722) via the radial support provided thereto by braided cable (730) to prevent push rod (710) from buckling. In other words, push rod (710) may have sufficient column strength to advance pusher member (166) distally, at least when push rod (710) is in the compressed state. In some versions, push rod (710) may also transmit tensile axial loads, such as for transmitting proximal motion from moveable member (128) to pusher member (166) to retract pusher member (166) proximally, via strands (722). In such cases, pull rod (702) may be omitted, and strands (722) may be sufficiently rigid in each radial direction to inhibit engaged pairs of strands (722) from skewing or otherwise shifting away from each other in a radial direction during application of compressive axial loads thereto in the absence of braided cable (730).

F. Sixth Exemplary Deflectable Firing Member

Figure 23A:
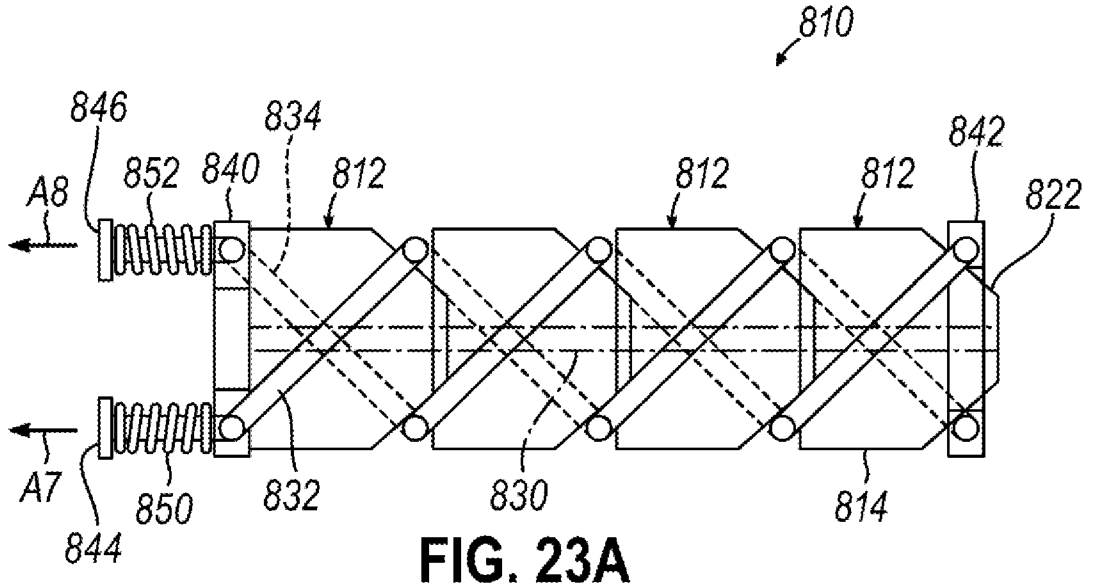
FIG. 23A depicts a side elevational view of another exemplary push rod for use with the surgical instrument of FIG. 4, showing the push rod in an undeflected state.
Figure 23B:
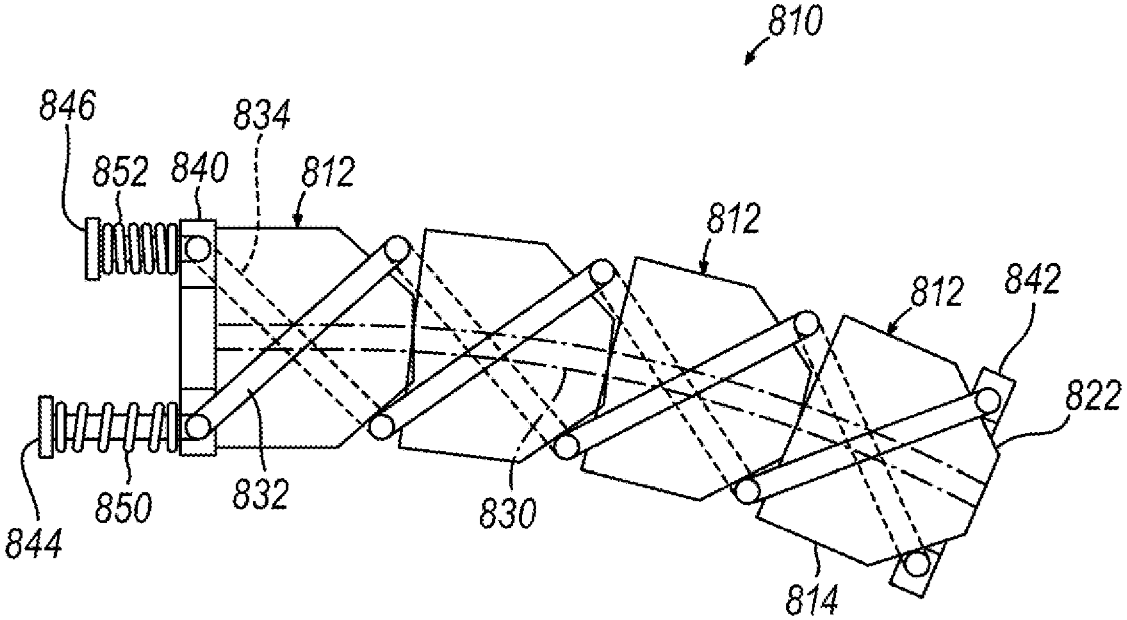
FIG. 23B depicts a side elevational view of the push rod of FIG. 23A, showing the push rod in a laterally deflected state.
Figure 24:
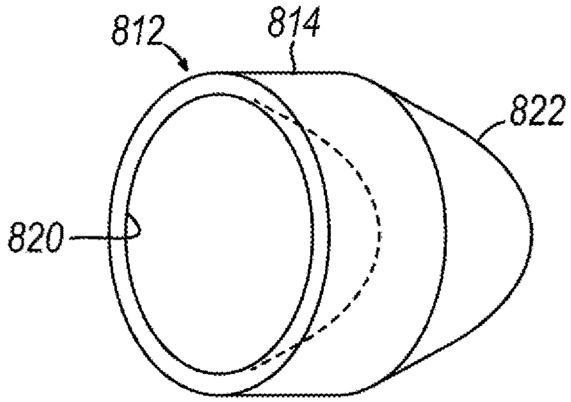
FIG. 24 depicts a perspective view of a link of the push rod of FIG. 23A.

FIGS. 23A-24 show another exemplary push rod (810) for use with surgical instrument (110) described above. Push rod (810) is similar to push rod (168) described above except as otherwise described below. In this regard, push rod (810) may operatively couple a pusher member (not shown), such as pusher member (166), with an actuation mechanism (not shown), such as moveable member (128), for transmitting proximal and/or distal motion between pusher member (166) and moveable member (128).

As shown in FIGS. 23A-23B, push rod (810) includes a plurality of segments in the form of individual links (812) flexibly stacked together in a columnar arrangement along a longitudinal axis, such as the longitudinal axis defined by shaft assembly (114). As best shown in FIG. 24, each link (812) includes a generally cylindrical hub (814), and further includes a generally conical proximal socket (820) extending distally from a proximal end of hub (814) and a generally conical distal nose (822) extending distally from a distal end of hub (814). Each socket (820) is tapered and/or rounded radially inwardly toward a distal apex, and each nose (822) is similarly tapered and/or rounded radially inwardly toward a distal apex such that the shape of each nose (822) is generally complementary to that of each socket (820). In this manner, the socket (820) of a relatively distal link (812) may matingly receive the nose (822) of a longitudinally-adjacent, relatively proximal link (812). In some versions, socket (820) of the proximal-most link (812) may define an input surface for receiving forces from moveable member (128) and nose (822) of the distal-most link (812) may define an output surface for transmitting such forces to pusher member (166). In the present version, each link (812) further includes a central bore (not shown) extending between the apexes of the respective socket (820) and nose (822), the purposes of which are described below. Links (812) may each be formed of any suitable material, such as a metal or polymer-based material. As described in greater detail below, sockets (820) may each cooperate with the respective nose (822) received therein to impart bending flexibility and/or axial stiffness to push rod (810).

As shown, push rod (810) further includes a central flexible shaft (830) extending longitudinally through the central bores of the stacked plurality of links (812). As described in greater detail below, flexible shaft (830) may cooperate with the central bores of links (812) to impart lateral misalignment (e.g., skew) resistance to push rod (810). Push rod (810) further includes first and second cables (832, 834), each wrapped helically about the stacked plurality of links (812) and extending distally from a proximal annular ring (840) to a distal annular ring (842) positioned at corresponding ends of the stacked plurality of links (812). In this regard, distal ring (842) may be seated against a radially outer surface of nose (822) of the distal-most link (812) and proximal ring (840) may be seated against the proximal end of the proximal-most link (812), such that the stacked plurality of links (812) is sandwiched between rings (840, 842). In some versions, one or both rings (840, 842) may be fixedly secured to the corresponding link (812). As described in greater detail below, first and second cables (832, 834) may cooperate with links (812) and rings (840, 842) to impart lateral misalignment (e.g., skew) resistance to push rod (810).

In the present version, first cable (832) is wrapped helically in a clockwise direction from a lateral lower region of proximal ring (840) to a lateral lower region of distal ring (842), and second cable (834) is wrapped helically opposite first cable (832) in a counterclockwise direction from a lateral upper region of distal ring (842) to a lateral upper region of proximal ring (840). Cables (832, 834) are each fixedly secured at their distal ends to distal ring (842) and are each fixedly secured at their proximal ends to first and second caps (844, 846), respectively, which are each positioned proximally of proximal ring (840), with intermittent portions of cables (832, 834) securely nested at periodic joints between longitudinally-adjacent pairs of links (812) (e.g., between a radially outer surface of nose (822) of the relatively proximal link (812) of each pair and a proximal end of the relatively distal link (812) of each pair). In this regard, cables (832, 834) each extend proximally through corresponding bores (not shown) in proximal ring (840) to the respective cap (844, 846), which is resiliently biased proximally away from proximal ring (840) by first and second compression springs (850, 852), respectively. It will be appreciated that caps (844, 846) may be resiliently biased proximally away from proximal ring (840) by any other suitable biasing member. In any event, such biasing of caps (844, 846) may assist in maintaining the respective cables (832, 834) in tension by pulling cables (832, 834) proximally, as indicated by arrows (A7, A8) in FIG. 23A. In some versions, generally helical grooves (not shown) may be provided on links (812) for receiving the respective cables (832, 834) to thereby hold or otherwise align the respective cables (832, 834) relative to links (812).

With continuing reference to FIGS. 23A-23B, at least a distal portion of push rod (810) is configured to transition between a natural state (FIG. 23A) and at least one laterally deflected state (FIG. 23B). In some versions, push rod (810) may be resiliently biased toward the natural state, such as via flexible shaft (830) and/or cables (832, 834).

As shown in FIG. 23B, at least the distal portion of push rod (810) may be deflectable relative to the longitudinal axis of shaft assembly (114). In this regard, flexible shaft (830) and/or cables (832, 834) may be sufficiently flexible to permit the distal portion of push rod (810) to deflect laterally away from the longitudinal axis via pivotable engagement between noses (822) and sockets (820) of longitudinally-adjacent links (812). While the distal portion of push rod (810) is shown deflecting laterally outwardly (e.g., downwardly) from the longitudinal axis, it will be appreciated that the distal portion of push rod (810) may deflect laterally from the longitudinal axis in any other direction. In this manner, push rod (810) may conform to or otherwise accommodate articulation of end effector (116) relative to the longitudinal axis defined by shaft assembly (114) (e.g., via any suitable wrist architecture of end effector (116)). Cables (832, 834) may be maintained in tension as described above to inhibit engaged pairs of noses (822) and sockets (820) from skewing or otherwise shifting away from each other in a lateral direction during application of compressive axial loads thereto. Flexible shaft (830) may also be sufficiently rigid to inhibit engaged pairs of noses (822) and sockets (820) from skewing or otherwise shifting away from each other in a lateral direction during application of compressive axial loads thereto. In this manner, push rod (810) may transmit compressive axial loads, such as for transmitting distal motion from moveable member (128) to pusher member (166) to advance pusher member (166) distally, via engaged pairs of noses (822) and sockets (820), while resisting lateral misalignment of noses (822) and sockets (820) via cables (832, 834) and/or flexible shaft (830) to prevent push rod (810) from budding. In other words, push rod (810) may have sufficient column strength to advance pusher member (166) distally, even when push rod (810) is in the deflected state. It will be appreciated that separate controls may be provided to apply additional tension to either cable (832, 834) based on the deflected state of push rod (810) and/or the magnitude of the compressive axial loads. In some versions, push rod (810) may also transmit tensile axial loads, such as for transmitting proximal motion from moveable member (128) to pusher member (166) to retract pusher member (166) proximally, via flexible shaft (830) and/or cables (832, 834).

G. Seventh Exemplary Deflectable Firing Member

Figure 25:
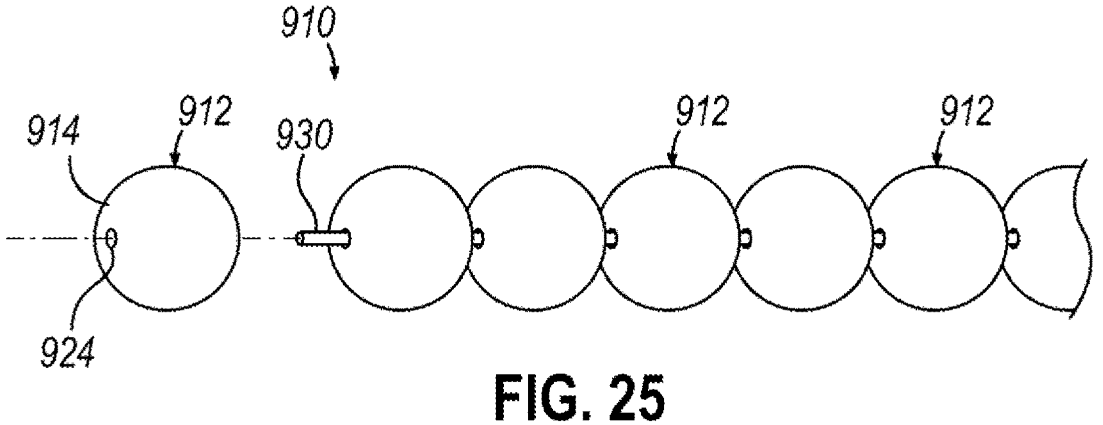
FIG. 25 depicts a partially disassembled perspective view of a distal portion of another exemplary push rod for use with the surgical instrument of FIG. 4.

FIG. 25 shows a distal portion of another exemplary push rod (910) for use with surgical instrument (110) described above. Push rod (910) is similar to push rod (168) described above except as otherwise described below. In this regard, push rod (910) may operatively couple a pusher member (not shown), such as pusher member (166), with an actuation mechanism (not shown), such as moveable member (128), for transmitting proximal and/or distal motion between pusher member (166) and moveable member (128).

As shown, push rod (910) includes a plurality of segments in the form of individual links (912) flexibly stacked together in a columnar arrangement along a longitudinal axis, such as the longitudinal axis defined by shaft assembly (114). Each link (912) includes a generally spherical body (914), such that a proximal rounded side of a relatively distal link (912) may abut a distal rounded side of a longitudinally-adjacent, relatively proximal link (912). In some versions, the proximal side of the proximal-most link (912) may define an input surface for receiving forces from moveable member (128) and the distal side of the distal-most link (912) may define an output surface for transmitting such forces to pusher member (166). In the present version, each link (912) further includes a central bore (924) extending between the proximal and distal sides, the purposes of which are described below. Links (912) may each be formed of any suitable material, such as a metal or polymer-based material.

As described in greater detail below, the rounded sides of longitudinally-adjacent links (912) may cooperate with each other to impart bending flexibility to push rod (910). Push rod (910) further includes a central cable (930) extending longitudinally through central bores (924) of the stacked plurality of links (912). As described in greater detail below, cable (930) may cooperate with central bores (924) of links (912) to impart lateral misalignment (e.g., skew) resistance to push rod (910).

It will be appreciated that at least a distal portion of push rod (910) is configured to transition between the natural state shown in FIG. 25 and at least one laterally deflected state (not shown), in a manner similar to that described above in connection with FIGS. 23A-23B. In some versions, push rod (910) may be resiliently biased toward the natural state, such as via cable (930).

For example, at least the distal portion of push rod (910) may be deflectable relative to the longitudinal axis of shaft assembly (114). In this regard, cable (930) may be sufficiently flexible to permit the distal portion of push rod (910) to deflect laterally away from the longitudinal axis via engagement between the rounded sides of longitudinally-adjacent pairs of links (912). In this manner, push rod (910) may conform to or otherwise accommodate articulation of end effector (116) relative to the longitudinal axis defined by shaft assembly (114) (e.g., via any suitable wrist architecture of end effector (116)). Cable (930) may be sufficiently rigid to inhibit engaged pairs of links (912) from skewing or otherwise shifting away from each other in a lateral direction during application of compressive axial loads thereto. In this manner, push rod (910) may transmit compressive axial loads, such as for transmitting distal motion from moveable member (128) to pusher member (166) to advance pusher member (166) distally, via engaged pairs of links (912), while resisting lateral misalignment of links (912) via cable (930) to prevent push rod (910) from buckling. In other words, push rod (910) may have sufficient column strength to advance pusher member (166) distally, even when push rod (910) is in the deflected state. In some versions, push rod (910) may also transmit tensile axial loads, such as for transmitting proximal motion from moveable member (128) to pusher member (166) to retract pusher member (166) proximally, via cable (930).

H. Eighth Exemplary Deflectable Firing Member

Figure 26:
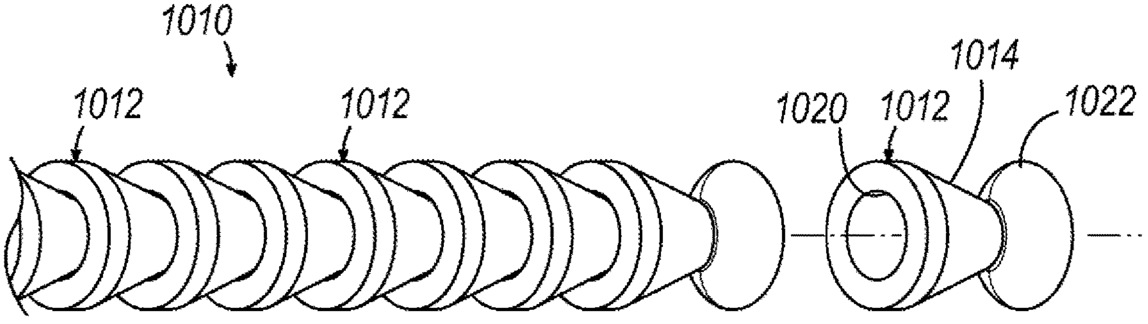
FIG. 26 depicts a partially disassembled perspective view of a distal portion of another exemplary push rod for use with the surgical instrument of FIG. 4.

FIG. 26 shows a distal portion of another exemplary push rod (1010) for use with surgical instrument (110) described above. Push rod (1010) is similar to push rod (168) described above except as otherwise described below. In this regard, push rod (1010) may operatively couple a pusher member (not shown), such as pusher member (166), with an actuation mechanism (not shown), such as moveable member (128), for transmitting proximal and/or distal motion between pusher member (166) and moveable member (128).

As shown, push rod (1010) includes a plurality of segments in the form of individual links (1012) flexibly stacked together in a columnar arrangement along a longitudinal axis, such as the longitudinal axis defined by shaft assembly (114). Each link (1012) includes a generally conical hub (1014), and further includes a generally hemispherical proximal socket (1020) extending distally from a proximal end of hub (1014) and a generally hemispherical distal nose (1022) extending distally from a distal end of hub (1014). Each socket (1020) is rounded radially inwardly toward the proximal end of hub (1014), and each nose (1022) is similarly rounded radially inwardly toward the distal end of hub (1014) such that the shape of each nose (1022) is generally complementary to that of each socket (1020). In this manner, the socket (1020) of a relatively distal link (1012) may matingly receive the nose (1022) of a longitudinally-adjacent, relatively proximal link (1012). In the example shown, each socket (1020) of a relatively distal link (1012) also partially receives the hub (1014) of the longitudinally-adjacent, relatively proximal link (1012). In some versions, socket (1020) of the proximal-most link (1012) may define an input surface for receiving forces from moveable member (128) and nose (1022) of the distal-most link (1012) may define an output surface for transmitting such forces to pusher member (166). Links (1012) may each be formed of any suitable material, such as a metal or polymer-based material. As described in greater detail below, sockets (1020) may each cooperate with the respective nose (1022) received therein to impart bending flexibility and/or axial stiffness to push rod (1010), while sockets (1020) may each cooperate with the respective hub (1014) partially received therein to impart lateral misalignment (e.g., skew) resistance to push rod (1010).

It will be appreciated that at least a distal portion of push rod (1010) is configured to transition between the natural state shown in FIG. 26 and at least one laterally deflected state (not shown), in a manner similar to that described above in connection with FIGS. 23A-23B. In some versions, push rod (1010) may be malleable from the natural state toward the deflected state.

For example, at least the distal portion of push rod (1010) may be deflectable relative to the longitudinal axis of shaft assembly (114). In this regard, sockets (1020) may each be sufficiently wider than the portion of the respective hub (1014) received therein to permit the distal portion of push rod (1010) to deflect laterally away from the longitudinal axis via pivotable engagement between noses (1022) and sockets (1020) of longitudinally-adjacent pairs of links (1012). In this manner, push rod (1010) may conform to or otherwise accommodate articulation of end effector (116) relative to the longitudinal axis defined by shaft assembly (114) (e.g., via any suitable wrist architecture of end effector (116)). The portion the respective hub (1014) received within each socket (1020) may be sufficiently wide to inhibit engaged pairs of noses (1022) and sockets (1020) from skewing or otherwise shifting away from each other in a lateral direction during application of compressive axial loads thereto. In this manner, push rod (1010) may transmit compressive axial loads, such as for transmitting distal motion from moveable member (128) to pusher member (166) to advance pusher member (166) distally, via engaged pairs of noses (1022) and sockets (1020), while resisting lateral misalignment of links (1012) via cooperation between hubs (1014) and sockets (1020) to prevent push rod (1010) from buckling or jackknifing. In other words, push rod (1010) may have sufficient column strength to advance pusher member (166) distally, even when push rod (1010) is in the deflected state. In some versions, push rod (1010) may also transmit tensile axial loads, such as for transmitting proximal motion from moveable member (128) to pusher member (166) to retract pusher member (166) proximally, via engaged pairs of noses (1022) and sockets (1020).

I. Ninth Exemplary Deflectable Firing Member

Figure 27:
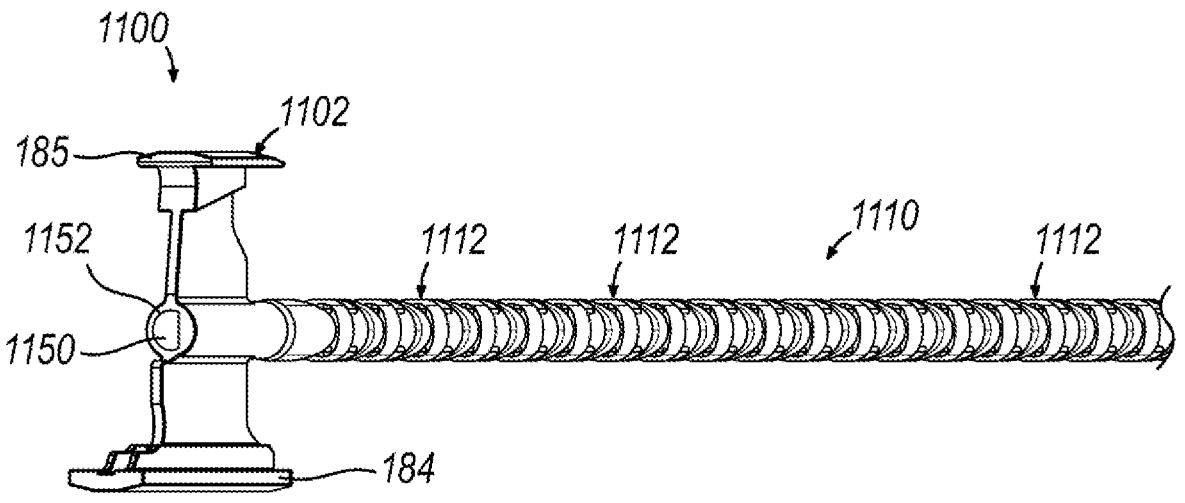
FIG. 27 depicts a perspective view of another exemplary driving assembly for use with the surgical instrument of FIG. 4.
Figure 28:
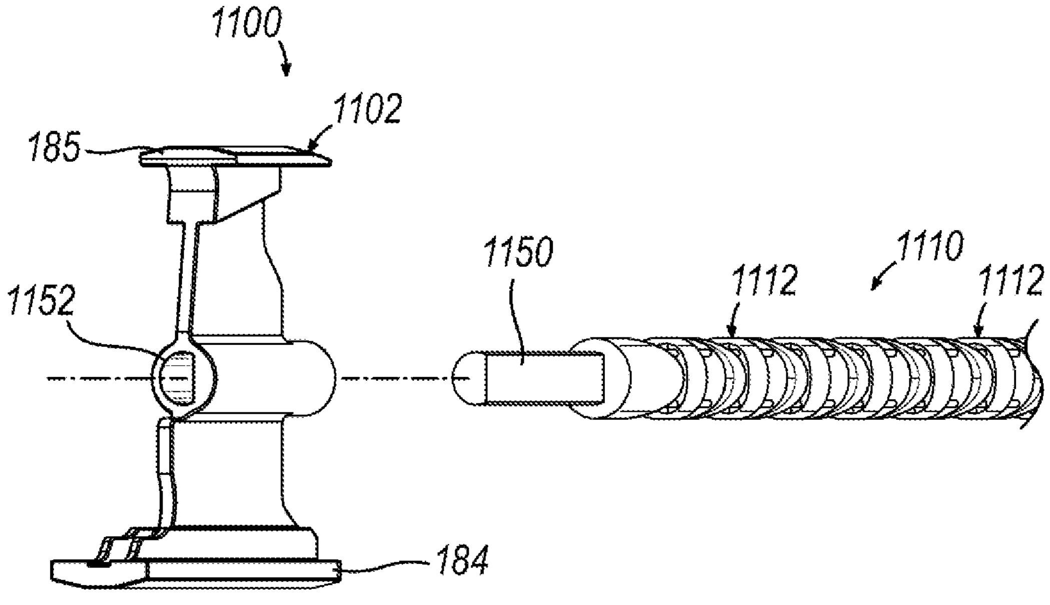
FIG. 28 depicts a partially disassembled perspective view of the driving assembly of FIG. 27.

FIGS. 27-28 show a driving assembly (1100) including a pusher member (1102) and another exemplary push rod (1110) for use with surgical instrument (110) described above. Driving assembly (1100) is similar to driving assembly (164) described above except as otherwise described below. In this regard, push rod (1110) may operatively couple pusher member (1102) with an actuation mechanism (not shown), such as moveable member (128), for transmitting distal motion between pusher member (1102) and moveable member (128).

As shown, push rod (1110) includes a plurality of segments in the form of individual links (1112) flexibly stacked together in a columnar arrangement along a longitudinal axis, such as the longitudinal axis defined by shaft assembly (114). Each link (1112) includes at least one proximal detent (not shown) and at least one distal pocket (not shown). In some versions, the shape of each detent is generally complementary to that of each pocket. In this manner, the pocket of a relatively proximal link (1112) may matingly receive the detent of a longitudinally-adjacent, relatively distal link (1112), while maintaining a slight separation therebetween. In some versions, links (1112) may each be 3D printed. As described in greater detail below, the pockets may each cooperate with the respective detent received therein to impart bending flexibility and/or axial stiffness to push rod (1110), while also cooperating with the respective detent to impart lateral misalignment (e.g., skew) resistance to push rod (1110). In the embodiment shown, push rod (1110) also includes a distal key (1150) extending distally from the distal-most link (1112) and having a generally truncated circular cross-sectional shape, the purpose of which is described below.

As shown, pusher member (1102) includes first and second flanges (184, 185) described above in connection with FIG. 8. Pusher member (1102) of the present version further includes a keyway (1152) having a generally truncated circular cross-sectional shape complementary to that of distal key (1150) of push rod (1110). In this manner, keyway (1152) may receive and frictionally engage distal key (1150) to thereby couple push rod (1110) to pusher member (1102) and, more particularly, to secure pusher member (1102) against rotation relative to push rod (1110) about the longitudinal axis of shaft assembly (114).

It will be appreciated that at least a distal portion of push rod (1110) is configured to transition between the natural state shown in FIG. 27, at least one laterally deflected state (not shown), and at least one longitudinally compressed state (not shown), in manners similar to those described above in connection with FIGS. 14A-14B, 17A-17B, and 23A-23B. In some versions, push rod (1110) may be resiliently biased toward the natural state.

For example, at least the distal portion of push rod (1110) may be deflectable relative to the longitudinal axis of shaft assembly (114). In this regard, the distal portion of push rod (1110) may be permitted to deflect laterally away from the longitudinal axis via pivotable engagement between detents and pockets of longitudinally-adjacent pairs of links (1112). For example, the detents may interact with the pockets to resist but not prevent pivoting between longitudinally-adjacent pairs of links (1112). In this manner, push rod (1110) may conform to or otherwise accommodate articulation of end effector (116) relative to the longitudinal axis defined by shaft assembly (114) (e.g., via any suitable wrist architecture of end effector (116)).

At least the distal portion of push rod (1110) may also be compressible along the longitudinal axis of shaft assembly (114). In this regard, the slight separation between detents and pockets of longitudinally-adjacent pairs of links (1112) may permit such detents and pockets of longitudinally-adjacent pairs of links (1112) to be urged into engagement with each other, while the detents may be sufficiently rigid to inhibit engaged pairs of detents and pockets from skewing or otherwise shifting away from each other in a lateral direction during application of compressive axial loads thereto. In this manner, push rod (1110) may transmit compressive axial loads, such as for transmitting distal motion from moveable member (128) to pusher member (1102) to advance pusher member (1102) distally, via engaged pairs of detents and pockets, while resisting lateral misalignment of engaged pairs of detents and pockets to prevent push rod (1110) from buckling. In other words, push rod (1110) may have sufficient column strength to advance pusher member (1102) distally, at least when push rod (1110) is in the compressed state. In some versions, push rod (1110) may also transmit tensile axial loads, such as for transmitting proximal motion from moveable member (128) to pusher member (1102) to retract pusher member (1102) proximally, via engaged pairs of detents and pockets.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapling instrument comprising: (a) a shaft assembly extending along a longitudinal axis to a distal end; (b) an end effector at the distal end of the shaft assembly, wherein the end effector includes: (i) a first jaw, (ii) a second jaw, the first and second jaws being operable to transition between an open state and a closed state, and (iii) a driving assembly translatable distally relative to the first jaw and the second jaw to thereby transition the first and second jaws from the open state to the closed state; and (c) a flexible firing member configured to selectively advance the driving assembly distally and retract the driving assembly proximally, wherein the flexible firing member includes: (i) a plurality of segments, (ii) at least one axial force transmission feature configured to transmit axial forces between the segments, and (iii) at least one lateral alignment feature configured to resist lateral misalignment of the segments.

Example 2

The surgical stapling instrument of Example 1, wherein the flexible firing member is deflectable laterally away from the longitudinal axis.

Example 3

The surgical stapling instrument of Example 2, wherein the flexible firing member further includes a push rod configured to selectively advance the driving assembly distally and retract the driving assembly proximally, wherein the at least one axial force transmission feature is presented by the push rod.

Example 4

The surgical stapling instrument of Example 3, wherein the at least one lateral alignment feature is presented by the push rod.

Example 5

The surgical stapling instrument of Example 4, wherein the push rod includes a plurality of slots, wherein the at least one axial force transmission feature includes proximal and distal surfaces of the slots.

Example 6

The surgical stapling instrument of Example 5, wherein the at least one lateral alignment feature includes bridges defined between the slots.

Example 7

The surgical stapling instrument of any of Examples 5 through 6, wherein the plurality of slots includes at least one a plurality of I-shaped slots, a plurality of linear slots, a plurality of step-shaped slots, or a plurality of hook-shaped slots.

Example 8

The surgical stapling instrument of any of Examples 3 through 7, wherein the push rod includes a mesh portion, wherein the at least one axial force transmission feature includes strands of the mesh portion.

Example 9

The surgical stapling instrument of any of Examples 3 through 8, wherein the push rod includes a plurality of links flexibly stacked together in a columnar arrangement.

Example 10

The surgical stapling instrument of Example 9, wherein the links each include a spherical body, wherein the at least one axial force transmission feature includes rounded proximal and distal surfaces of the links.

Example 11

The surgical stapling instrument of any of Examples 9 through 10, wherein the links each include a conical body, wherein the at least one axial force transmission feature includes proximal sockets and distal noses of the links.

Example 12

The surgical stapling instrument of any of Examples 9 through 11, wherein the at least one lateral alignment feature includes at least one cable engaged with the links.

Example 13

The surgical stapling instrument of any of Examples 4 through 12, wherein the flexible firing member further includes a pull rod configured to retract the driving assembly proximally, wherein the pull rod is slidably received within the push rod, wherein the at least one lateral alignment feature is presented by the pull rod.

Example 14

The surgical stapling instrument of Example 13, wherein the at least one lateral alignment feature includes a radially outer surface of the pull rod configured to radially support the push rod.

Example 15

The surgical stapling instrument of any of Examples 1 through 14, wherein the flexible firing member further includes a distal key, wherein the driving assembly includes a keyway configured to receive and frictionally engage the distal key to secure the driving assembly against rotation relative to the flexible firing member about the longitudinal axis.

Example 16

A surgical stapling instrument comprising: (a) a shaft assembly extending along a longitudinal axis to a distal end; (b) an end effector at the distal end of the shaft assembly, wherein the end effector includes: (i) a first jaw, (ii) a second jaw, the first and second jaws being operable to transition between an open state and a closed state, the first and second jaws being further operable to staple tissue, and (iii) a driving assembly translatable distally relative to the first jaw and the second jaw to thereby transition the first and second jaws from the open state to the closed state; and (c) a flexible push rod configured to selectively advance the driving assembly distally, wherein the flexible push rod includes: (i) a cylindrical tube, (ii) at least one pair of diametrically-opposed slots extending circumferentially about respective portions of the cylindrical tube, each slot including a proximal surface and a distal surface configured to selectively contact each other for transmitting axial forces therebetween, and (iii) a pair of diametrically-opposed bridges extending circumferentially between the pair of diametrically-opposed slots, wherein the bridges are configured to resist lateral misalignment of the proximal and distal surfaces from each other.

Example 17

The surgical stapling instrument of Example 16, wherein the at least one pair of diametrically-opposed slots includes a pair of diametrically-opposed slots, wherein the at least one pair of diametrically-opposed bridges includes a pair of diametrically-opposed slots extending circumferentially between the pair of diametrically-opposed slots.

Example 18

The surgical stapling instrument of Example 17, wherein the at least one pair of diametrically-opposed slots further includes a pair of diametrically-opposed slots longitudinally spaced apart from the pair of diametrically-opposed slots, wherein the at least one pair of diametrically-opposed bridges further includes a pair of diametrically-opposed slots extending circumferentially between the pair of diametrically-opposed slots.

Example 19

A surgical stapling instrument comprising: (a) a shaft assembly extending along a longitudinal axis to a distal end; (b) an end effector at the distal end of the shaft assembly, wherein the end effector includes: (i) a first jaw, (ii) a second jaw, the first and second jaws being operable to transition between an open state and a closed state, the first and second jaws being further operable to staple tissue, and (iii) a driving assembly translatable distally relative to the first jaw and the second jaw to thereby transition the first and second jaws from the open state to the closed state; and (c) a flexible push rod configured to selectively advance the driving assembly distally through the second jaw, wherein the flexible push rod includes: (i) a plurality of links stacked together in a columnar arrangement, each link including a proximal socket and a distal nose configured to be received within the proximal socket of an adjacent link for transmitting axial forces therebetween, and (ii) at least one cable engaged with the links and configured to resist lateral misalignment of the links from each other.

Example 20

The surgical stapling instrument of Example 19, wherein the at least one cable includes a pair of cables wrapped about the plurality of links.

IV. Miscellaneous

Any one or more of the teachings, expressions, embodiments, examples, etc. described herein may be combined with any one or more of the teachings, expressions, embodiments, examples, etc. described in U.S. Pat. No. 9,060,770, entitled "Robotically-Driven Surgical Instrument with E-Beam Driver," issued Jun. 23, 2015, the disclosure of which is hereby incorporated by reference herein in its entirety.

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed Aug. 16, 2021 issued as U.S. Pat. No. 12,102,321 on Oct. 1, 2024; U.S. patent application Ser. No. 17/402,675, entitled "Multi-Threshold Motor Control Algorithm for Powered Surgical Stapler," filed Aug. 16, 2021 issued as U.S. Pat. No. 11,992,209 on May 28, 2024; U.S. patent application Ser. No. 17/402,677, entitled "Variable Response Motor Control Algorithm for Powered Surgical Stapler," filed Aug. 16, 2021, issued as U.S. Pat. No. 11,944,297 on Apr. 2, 2024; U.S. patent application Ser. No. 17/402,279, entitled "Powered Surgical Stapler Having Independently Operable Closure and Firing Systems," filed Aug. 16, 2021, issued as U.S. Pat. No. 11,779,332 on Oct. 10, 2023; U.S. patent application Ser. No. 17/402,695, entitled "Firing System Features for Surgical Stapler," filed Aug. 16, 2021, issued as U.S. Pat. No. 12,213,668 on Feb. 4, 2025; U.S. patent application Ser. No. 17/402,703, entitled "Multiple-Sensor Firing Lockout Mechanism for Powered Surgical Stapler," filed Aug. 16, 2021 issued as U.S. Pat. No. 11,992,210 on May 28, 2024; U.S. patent application Ser. No. 17/402,703, entitled "Proximally Located Firing Lockout Mechanism for Surgical Stapler," filed Aug. 16, 2021 issued as U.S. Pat. No. 11,957,336 on Apr. 16, 2024; U.S. patent application Ser. No. 17/402,720, entitled "Cartridge-Based Firing Lockout Mechanism for Surgical Stapler," filed Aug. 16, 2021 issued as U.S. Pat. No. 12,011,164 on Jun. 18, 2024; U.S. patent application Ser. No. 17/402,732, entitled "Sled Restraining Member for Surgical Stapler," filed Aug. 16, 2021, issued as U.S. Pat. No. 11,986,182 on May 21, 2024; U.S. patent application Ser. No. 17/402,738, entitled "Firing Member Tracking Feature for Surgical Stapler," filed Aug. 16, 2021, issued as U.S. Pat. No. 12,171,428 on Dec. 24, 2024; U.S. patent application Ser. No. 17/402,744, entitled "Adjustable Power Transmission Mechanism for Powered Surgical Stapler," filed Aug. 16, 2021 issued as U.S. Pat. No. 12,029,508 on Jul. 9, 2024; and/or U.S. patent application Ser. No. 17/402,749, entitled "Firing Bailout System for Powered Surgical Stapler," filed Aug. 16, 2021, issued as U.S. Pat. No. 12,089,842 on Sep. 17, 2024. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapling instrument comprising:
(a) a shaft assembly extending along a longitudinal axis to a distal end;
(b) an end effector at the distal end of the shaft assembly, wherein the end effector includes:
(i) a first jaw,
(ii) a second jaw, the first and second jaws being operable to transition between an open state and a closed state, and
(iii) a driving assembly translatable distally relative to the first jaw and the second jaw to thereby transition the first and second jaws from the open state to the closed state; and
(c) a flexible firing member configured to selectively advance the driving assembly distally and retract the driving assembly proximally, wherein the flexible firing member includes:
(i) a plurality of segments arranged along the longitudinal axis such that the plurality of segments includes a proximal segment and a distal segment that is entirely distal of the proximal segment,
(ii) at least one axial force transmission feature configured to transmit axial forces between the segments, and
(iii) at least one lateral alignment feature configured to resist lateral misalignment of the segments, wherein the at least one lateral alignment feature includes a pair of diametrically-opposed lateral alignment features, wherein the pair of diametrically-opposed lateral alignment features includes:
(A) a first lateral alignment feature, and
(B) a second lateral alignment feature disposed opposite the first lateral alignment feature relative to a diameter of the flexible firing member,
wherein the at least one axial force transmission feature includes proximal and distal surfaces of at least one slot, wherein the at least one slot includes a pair of longitudinal slot end portions and an intermediate slot portion extending circumferentially therebetween, wherein the intermediate slot portion defines the proximal and distal surfaces, wherein each longitudinal slot end portion of the pair of longitudinal slot end portions extends both proximally and distally farther along the longitudinal axis relative to the intermediate slot portion such that a width of each longitudinal slot end portion is greater than a width of the intermediate slot portion.

2. The surgical stapling instrument of claim 1, wherein the flexible firing member is deflectable laterally away from the longitudinal axis.

3. The surgical stapling instrument of claim 2, wherein the flexible firing member further includes a push rod configured to selectively advance the driving assembly distally and retract the driving assembly proximally, wherein the at least one axial force transmission feature is presented by the push rod.

4. The surgical stapling instrument of claim 3, wherein the at least one lateral alignment feature is presented by the push rod.

5. The surgical stapling instrument of claim 4, wherein the push rod includes a plurality of slots.

6. The surgical stapling instrument of claim 5, wherein the at least one lateral alignment feature includes bridges defined between the slots.

7. The surgical stapling instrument of claim 5, wherein the plurality of slots includes a plurality of I-shaped slots.

8. The surgical stapling instrument of claim 4, wherein the flexible firing member further includes a pull rod configured to retract the driving assembly proximally, wherein the pull rod is slidably received within the push rod, wherein the at least one lateral alignment feature is presented by the pull rod.

9. The surgical stapling instrument of claim 8, wherein the at least one lateral alignment feature includes a radially outer surface of the pull rod configured to radially support the push rod.

10. The surgical stapling instrument of claim 3, wherein the push rod includes a mesh portion, wherein the at least one axial force transmission feature includes strands of the mesh portion.

11. The surgical stapling instrument of claim 3, wherein the push rod includes a plurality of links flexibly stacked together in a columnar arrangement.

12. The surgical stapling instrument of claim 11, wherein the plurality of links each include a spherical body, wherein the at least one axial force transmission feature includes rounded proximal and distal surfaces of the links.

13. The surgical stapling instrument of claim 11, wherein the plurality of links each include a conical body, wherein the at least one axial force transmission feature includes proximal sockets and distal noses of the links.

14. The surgical stapling instrument of claim 11, wherein the at least one lateral alignment feature includes at least one cable engaged with the plurality of links.

15. The surgical stapling instrument of claim 1, wherein the flexible firing member further includes a distal key, wherein the driving assembly includes a keyway configured to receive and frictionally engage the distal key to secure the driving assembly against rotation relative to the flexible firing member about the longitudinal axis.

16. The surgical stapling instrument of claim 1, wherein the at least one axial force transmission feature includes a pair of diametrically-opposed axial force transmission features.

17. A surgical stapling instrument comprising:
(a) a shaft extending along a longitudinal axis to a distal end;
(b) an end effector operatively coupled with the shaft, wherein the end effector includes:
(i) a first jaw,
(ii) a second jaw, the first and second jaws being operable to transition between an open state and a closed state, the first and second jaws being further operable to staple tissue, and
(iii) a driving assembly translatable distally relative to the first jaw and the second jaw to thereby transition the first and second jaws from the open state to the closed state; and (c) a flexible push rod configured to selectively advance the driving assembly distally, wherein the flexible push rod includes:
(i) a cylindrical tube,
(ii) at least one pair of diametrically-opposed slots extending circumferentially about respective portions of the cylindrical tube, each slot including a proximal surface and a distal surface configured to selectively contact each other for transmitting axial forces therebetween, wherein the at least one pair of diametrically-opposed slots includes:
(A) a first slot, and
(B) a second slot disposed opposite the first slot relative to a diameter of the flexible push rod, and
(iii) at least one pair of diametrically-opposed bridges extending circumferentially between the pair of diametrically-opposed slots, wherein the bridges are configured to resist lateral misalignment of the proximal and distal surfaces from each other, wherein the at least one pair of diametrically-opposed bridges includes:
(A) a first bridge, and
(B) a second bridge disposed opposite the first bridge relative to the diameter of the flexible push rod,
wherein the first slot includes a pair of longitudinal slot end portions and an intermediate slot portion extending circumferentially therebetween, wherein the intermediate slot portion defines the proximal and distal surfaces of the first slot, wherein each longitudinal slot end portion of the pair of longitudinal slot end portions extends both proximally and distally farther along the longitudinal axis relative to the intermediate slot portion such that a width of each longitudinal slot end portion is greater than a width of the intermediate slot portion.

18. The surgical stapling instrument of claim 17, wherein the at least one pair of diametrically-opposed slots includes a first pair of diametrically-opposed slots, wherein the at least one pair of diametrically-opposed bridges includes a first pair of diametrically-opposed bridges extending circumferentially between the first pair of diametrically-opposed slots.

19. The surgical stapling instrument of claim 18, wherein the at least one pair of diametrically-opposed slots further includes a second pair of diametrically-opposed slots longitudinally spaced apart from the first pair of diametrically-opposed slots, wherein the at least one pair of diametrically-opposed bridges further includes a second pair of diametrically-opposed slots extending circumferentially between the second pair of diametrically-opposed slots.

20. A surgical stapling instrument comprising:
(a) a shaft extending along a longitudinal axis to a distal end;
(b) an end effector operatively coupled with the shaft, wherein the end effector includes:
(i) a first jaw,
(ii) a second jaw, the first and second jaws being operable to transition between an open state and a closed state, and
(iii) a driving assembly translatable distally relative to the first jaw and the second jaw to thereby transition the first and second jaws from the open state to the closed state; and
(c) a flexible firing member configured to selectively advance the driving assembly distally and retract the driving assembly proximally, wherein the flexible firing member includes:
(i) first and second segments arranged along the longitudinal axis such that the second segment is entirely distal of the first segment,
(ii) at least one slot defined between the first and second segments, wherein the at least one slot includes proximal and distal surfaces, the proximal and distal surfaces being configured to cooperate with each other to transmit axial forces between the first and second segments, and
(iii) at least one bridge defined between the first and second segments, the at least one bridge being configured to resist lateral misalignment of the segments,
wherein the at least one slot is I-shaped, wherein the at least one slot includes a pair of longitudinal slot end portions and an intermediate slot portion extending circumferentially therebetween, wherein the intermediate slot portion defines the proximal and distal surfaces, wherein each longitudinal slot end portion of the pair of longitudinal slot end portions extends both proximally and distally farther along the longitudinal axis relative to the intermediate slot portion such that a width of each longitudinal slot end portion is greater than a width of the intermediate slot portion,
wherein the at least one bridge extends circumferentially between the pair of longitudinal slot end portions.

* * * * *